United States Patent
Li

(10) Patent No.: US 10,143,626 B2
(45) Date of Patent: Dec. 4, 2018

(54) CONTROLLED RELEASE DOSAGE FORM

(71) Applicant: TRIASTEK, INC., Nanjing (CN)

(72) Inventor: Xiaoling Li, Dublin, CA (US)

(73) Assignee: TRIASTEK, INC., Nanjing (CN)

( * ) Notice: Subject to any disclaimer, the term of this patent is extended or adjusted under 35 U.S.C. 154(b) by 13 days.

(21) Appl. No.: 15/857,724

(22) Filed: Dec. 29, 2017

(65) Prior Publication Data

US 2018/0116911 A1    May 3, 2018

Related U.S. Application Data

(63) Continuation of application No. PCT/US2017/031446, filed on May 5, 2017.

(60) Provisional application No. 62/332,018, filed on May 5, 2016.

(51) Int. Cl.
*A61K 9/20* (2006.01)
*A61J 3/07* (2006.01)
*A61M 31/00* (2006.01)

(52) U.S. Cl.
CPC ............ *A61J 3/07* (2013.01); *A61K 9/2013* (2013.01); *A61K 9/2022* (2013.01); *A61K 9/2072* (2013.01); *A61K 9/2095* (2013.01); *A61M 31/002* (2013.01)

(58) Field of Classification Search
CPC .................................................... A61K 9/2031
See application file for complete search history.

(56) References Cited

U.S. PATENT DOCUMENTS 1,356,544 A * 10/1920 Miller ........................ A61J 3/07
424/43
5,902,605 A * 5/1999 Dong ................... A61K 9/0004
424/438

* cited by examiner

*Primary Examiner* — Benjamin J Packard
(74) *Attorney, Agent, or Firm* — Jun He Law Offices P.C.; James J. Zhu

(57) ABSTRACT

The present invention generally relates to a pharmaceutical dosage form and controlled release of biologically active agents, diagnostic agents, reagents, cosmetic agents, and agricultural/insecticide agents. In one embodiment, the dosage form has a substrate that forms a compartment, wherein the substrate includes at least a first piece and a second piece, wherein the first piece operably links to the second piece. The dosage form contains a drug content that is loaded into the compartment. The dosage form also has a releaser operably linked to the substrate which upon contact with water or body fluid is capable of separating the first and second piece to open the compartment and release the drug content.

16 Claims, 5 Drawing Sheets

CONTROLLED RELEASE DOSAGE FORM

CROSS-REFERENCE TO RELATED APPLICATIONS

This application is a continuation of PCT/US2017/031446, filed on May 5, 2017, which claims priority to U.S. provisional patent application No. 62/332,018, filed May 5, 2016, the disclosure of which is incorporated herein by reference.

FIELD OF THE INVENTION

The present invention generally relates to a pharmaceutical dosage form and controlled release of biologically active agents, diagnostic agents, reagents, cosmetic agents, and agricultural/insecticide agents.

BACKGROUND

Oral administration is the most popular route for systemic effects due to its ease of ingestion, pain avoidance, versatility and patient compliance. Among all dosage forms tablet is most commonly used because of its benefits in terms of manufacturing, packaging and shipping, and easy to identify and swallow. After being administered into a living organism, a tablet undergoes interplay with the body in exerting pharmaceutical effects. The active pharmaceutical ingredient must be released from the tablet before being absorbed into the blood circulation. The pharmaceutical ingredient then disperses, disintegrates or dissolves throughout the fluids and tissues of the body. During drug absorption, disposition, metabolism, and elimination process, dosage forms play a critical role in determining the release profile and bioavailability of the drugs.

In some cases, pulsatile drug release is required, as the drug is released completely after defined lag time. Pulsatile drug release is time and site-specific drug delivery, thus providing spatial and temporal delivery and increasing patient compliance. In certain cases, multiple-pulse drug release is desired to achieve pulsatile release for more than one drug or more than one time. Manufacturing such pulsatile drug delivery system, however, is challenging. Therefore, there is a continuing needs for developing dosage forms that provides controlled or programmable drug delivery systems, which may offer desired drug plasma levels, reduced side effects as well as improved patient compliance.

BRIEF SUMMARY OF THE INVENTION

In one aspect, the present disclosure provides a solid pharmaceutical dosage form. In one embodiment, the dosage form comprises a substrate that forms a compartment, wherein the substrate comprises at least a first piece and a second piece, wherein the first piece operably links to the second piece. The dosage form comprises a drug content that is loaded into the compartment. The dosage form also comprises a releaser operably linked to the substrate which upon contact with water or body fluid is capable of separating the first and second piece to open the compartment and release the drug content.

In one embodiment, the compartment disclosed herein has an aperture which is sealed by the releaser. In certain embodiments, the releaser disclosed herein comprises a hydrogel.

In certain embodiments, the releaser comprises an effervescent material loaded in the compartment.

In certain embodiments, the substrate disclosed herein is made from a thermoformable material.

In certain embodiments, the substrate disclosed herein has a shape of a square column or a cylindrical column.

In certain embodiments, the compartment disclosed herein has a shape of a square column or a cylindrical column.

In certain embodiments, the drug content disclosed herein comprises an active pharmaceutical ingredient (API). In certain embodiments, the API is selected from the groups consisting of local anesthetics, antiepileptic drugs and anticonvulsants, anti-alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, immunomodulators, and cosmetically active agents.

In certain embodiments, the drug content disclosed herein further comprises an excipient associated with the API.

In another aspect, the present disclosure provides a solid pharmaceutical dosage form for multiple-pulse drug release. In one embodiment, the dosage form comprises a first substrate that forms a first compartment, wherein the first substrate comprises at least a first piece and a second piece, wherein the first piece operably links to the second piece. The dosage form contains a first drug content loaded into the first compartment. The dosage dosage form also comprises a first releaser operably linked to the first substrate which upon contact with water or body fluid is capable of separating the first and second piece to open the first compartment and release the first drug content. The dosage form further comprises a second substrate that forms a second compartment, wherein the second substrate comprises at least a third piece and a fourth piece, wherein the third piece operably links to the fourth piece. The dosage form contains a second drug content loaded into the second compartment. The dosage form has a second releaser operably linked to the second substrate which upon contact with water is capable of separating said third and fourth piece to release the second drug content. The first substrate is operably linked to the second substrate, and the first compartment is separated from the second compartment. The second releaser is accessible to water or body fluid only after the first and second pieces are separated and the first compartment is opened.

In one embodiment, the first compartment has a first aperture which is sealed by the first releaser. In one embodiment, the second compartment has a second aperture which is sealed by the second releaser. In one embodiment, the second aperture is enclosed in the first compartment.

In certain embodiments, the first drug content is the same as the second drug content. In certain embodiments, the first drug content is different from the second drug content.

In certain embodiments, the first releaser and the second releaser are made of the same material. In certain embodiments, the first releaser is made of a first material and the second releaser is made of a second material, wherein the first material is different from the second material.

In certain embodiments, the first substrate stacks on the second substrate.

These and other features, aspects, and advantages of the present invention will become better understood with regard to the following description, appended claims and accompanying drawings.

DESCRIPTION OF THE INVENTION

Figure 1A:
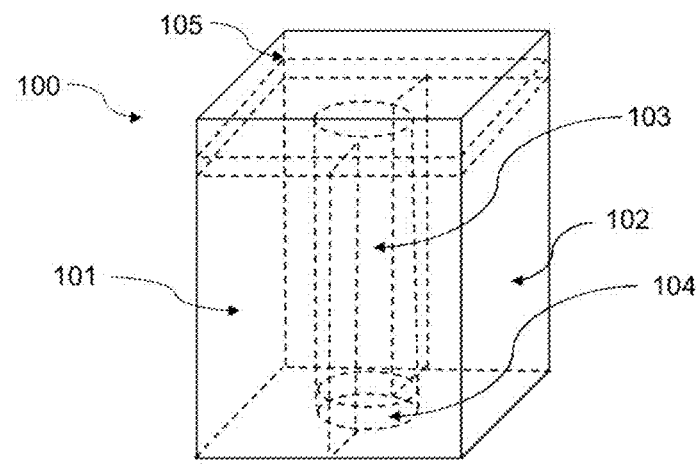
FIG. 1A shows a top perspective view of a solid pharmaceutical dosage form according to an embodiment of the invention.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definition

The following definitions are used in the disclosure:

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

As used herein, "compartment" refers to a space, part or room marked or partitioned off by the substrate. A compartment can be closed or be open (e.g., having an aperture or a passageway). A compartment can be of any geometry suitable for loading drug contents. In certain embodiments, the compartment has a shape selected from the group consisting of a pie shape, a cone shape, a pyramid shape, a cylindrical shape, a cubic or cuboidal shape, a triangular or polygonal prism shape, a tetrahedron and a combination thereof.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

As used herein, the term "drug content" refers to a composition comprising one or more active ingredient, including active pharmaceutical ingredient (API), cosmetic agent, biological agent, diagnostic agent and reagent for scientific experiments.

As used herein, the term "releaser" refers to a structure or substance that upon contact with water or body fluid can expand in volume or generate force (e.g., by generating gas) to disintegrate the substrate as disclosed herein, e.g., by separating the pieces of the substrate, and open the compartment.

As used herein, "substrate" refers to a structure in which a drug content is enclosed or embedded. The substrate of a dosage form of the instant invention can be of any size and shape that are suitable for oral administration. In certain embodiments, the substrate is a flat round tablet having a diameter of around 2 mm, 3 mm, 4 mm, 5 mm, 6 mm, 7 mm, 8 mm, 9 mm, 10 mm, 11 mm 12 mm. In certain embodiments, the substrate is an oval tablet having a dimension of around a mm×b mm, wherein a is 5 to 15 and b is 2 to 10. In certain embodiments, the substrate has a capsule shape.

As used herein, a "piece" of the substrate as disclosed herein refers to a part of the substrate that has a pre-defined structure (i.e., not amorphous or in the form of particles). In certain embodiments, the substrate has at least two pieces, e.g., 2, 3, 4, 5, 6 or more pieces. In certain embodiments, each piece has about the same volume. In certain embodiments, each pieces has about a half, one third, one fourth of the volume of the substrate. In certain embodiments, each piece has about the same geometrical shape. In certain embodiments, multiple pieces are operably linked to form a compartment.

Controlled Release Dosage Form

In one aspect, the present disclosure provides a solid pharmaceutical dosage form for oral administration. In one embodiment, the dosage form comprises a substrate that forms a compartment, wherein the substrate comprises at least a first piece and a second piece, wherein the first piece operably links to the second piece. The dosage form comprises a drug content that is loaded into the compartment. The dosage form also comprises a releaser operably linked to the substrate which upon contact with water or body fluid is capable of separating the first and second piece to open the compartment and release the drug content.

In certain embodiments, the substrate is made of a hydrophilic polymer (e.g., hydroxypropylmethylcellulose (HPMC) and poly(ethylene oxide) (PEO)), a hydrophobic polymer (e.g., ethylcelluose (EC)), a swellable polymer, a non-swellable polymer, a porous polymer, a non-porous polymer, an erodible polymer, or a non-erodible polymer.

In certain embodiments, the substrate is made of a thermoplastic material. As used herein, a "thermoplastic material" refers to a material having the ability to be shaped using heat and pressure. In certain embodiments, the thermoplastic materials may, for example, be hydrophilic, gel-forming materials, from which drug content release proceeds mainly by diffusion, or hydrophobic materials, from which drug content release proceeds mainly by diffusion from the pores in the substrate. Polymers, particularly cellulose ethers, cellulose esters and/or acrylic resins can be used as hydrophilic thermoplastic materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are suitable for use as thermoplastic materials. Physiologically acceptable, hydrophobic materials that are known to the person skilled in the art, such as mono- or diglycerides of C12-C30 fatty acids and/or C12-C30 fatty alcohols and/or waxes or mixtures thereof may be used as thermoplastic material. Substrate prepared from hydrophobic materials, such as hydrophobic polymers, waxes, fats, long-chain fatty acids, fatty alcohols or corresponding esters or ethers or mixtures thereof are also envisioned.

In certain embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), hydroxyl propyl cellulose (HPC), Polyoxyl 40 Hydrogenerated Castor Oil, Methyl cellulose (MC), Ethyl cellulose (EC), Poloxamer, hydroxypropyl methylcellulose phthalate (HPMCP), Poloxamer, Hydrogenated Castor & Soybean Oil, GlyEUceryl Palmitostearate, Carnauba Wax, polylactic acid (PLA), polyglycolic acid (PGA), Cellulose acetate butyrate (CAB), Colloidal Silicon, Dioxide, Sucrose, Glucose, Polyvinyl Acetate Phthalate (PVAP), Eudragit RS PO, Triethyl citrate (TEC) and a combination thereof.

As disclosed herein, the substrate of the dosage form has at least two pieces, e.g., 2, 3, 4, 5, 6 or more pieces. The piece of the substrate refers to a part of the substrate that has a pre-defined structure (i.e., not amorphous or in the form of particles). In certain embodiments, each piece has about the same volume. In certain embodiments, each pieces has about a half, one third, one fourth of the volume of the substrate. In certain embodiments, each piece has about the same geometrical shape. In certain embodiments, multiple pieces are operably linked to form a compartment. In certain embodiments, the substrate of the dosage form has a shape of a polygonal (e.g, a square, a pentagonal, etc) or cylindrical column that forms a compartment inside, and the pieces of the substrate form the wall of the column.

The pieces of the substrate are operably linked through a manner that can be broken apart with the help of the releaser as disclosed herein (e.g, when the releaser contact upon water to expand in volume or generate force or pressure). In certain embodiments, the pieces of the substrate is linked though very thin structure. In certain embodiments, the linking structure is about 0.1, 0.2, 0.3, 0.4, 0.5, 0.6, 0.7, 0.8, 0.9 or 1 mm thick. In certain embodiments, the linking structure is in a shape that prevents water or body fluid penetrate into the compartment. In certain embodiments the structure that links the pieces is made of the same material as the pieces. In certain embodiments, the linking structure is made of different material from that of the pieces of the substrate. In certain embodiments, the linking structure is made in the same 3D printing process during the manufacture of the dosage form. In certain embodiments, the pieces of the substrate are made before they are linked to form the compartment.

In certain embodiments, the drug content contains at least one API. As used herein, an API refers to an ingredient in a pharmaceutical drug that is biologically active. In certain embodiments, the API is selected from the groups consisting of local anesthetics, antiepileptic drugs and anticonvulsants, anti-Alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, anti-tuberculous drugs, antiviral drugs, antineoplasm drugs, immune-modulators, cosmetically active agents, traditional Chinese medicine (TCM) and TCM extracts.

In certain embodiments, the API is selected from the groups consisting of (R)-folitixorin, lidocaine, 11-di-deutero-ethyllinoleate, 16-dehydro-pregnenolone, 17-beta-estradiol, 2-iminobiotin, 3,5-diiodothyropropionicacid, 5-fluoro-2-deoxycytidine, 6-mercaptopurine, edotreotide, abacavir, abalone haemocyanin, abametapir, abediterol, abemaciclib, abexinostat, abiraterone, acalabrutinib, acamprosate, acamprosatecalcium, acarbose, acebilustat, aceclidine, aceclofenac, acehytisine hydrochloride, acemannan, aceneuramic acid, acetaminophen, acetylcysteine, acetylkitasamycin, acetyl-L-carnitinehydrochloride, acetylsalicylicacid, aciclovir, acipimox, acitazanolast, acitretin, aclidinium, aclidinium bromide, acolbifene, acorafloxacin, acotiamide, acrivastine, actarit, adapalene, adapalene, adefovirdipivoxil, ademetionine, adoair, afatinib, afimoxifene, afuresertib, agomelatine, aildenafilcitrate, aladorian, alalevonadifloxacin mesylate, alarelin acetate, alatrofloxacin mesylate, albendazole, albuterol sulfate, albuterpenoids, alcaftadine, aldoxorubicin, alectinib, alendronate, alendronate sodium, alendronate sodiumhydrate, alendronic acid, alfacalcidol, alfaxalone, alfentanil, alfuzosin, alisertib, aliskiren, alisporivir, alitretinoin, allantoin, allisartanisoproxil, allopurinol, almotriptan, alogliptin, alogliptin benzoate, alosetron, alpelisib, alphaketoglutarate, alphalipoic acid, alpha-1antitrypsin, alpha-cyclodextrin-stabilized sulforaphane, alprazolam, alprostadil, alprostadil alfadex, altiratinib, altretamine, altropane, aluminum sulfate, alvimopan, alvocidib, amantadine, amantadine hydrochloride, ambrisentan, ambroxol, ambroxol hydrochloride, amcasertib, amfetamine, amfetamine polistirex, amifampridine, amifampridine phosphate, amifostine, amikacin, amiloride, aminolevulinic, aminolevulinic acid, aminolevulinic acid hydrochloride, aminopterin, amiodarone, amiselimod, amisulpride, amitifadine hydrochloride, amitriptyline, amlexanox, amlodipine, amlodipine, amlodipinebesilate, amlodipine besylate, amlodipine camsylate, amlodipine maleate, amlodipine nicotinate, amlodipine orotate, ammonium lactate, amodiaquine, amorolfine, amosulalol, amoxicillin, amoxicillin hydrate, amphetamine, amphetamine aspartate, amphetamine sulfate, amphotericinB, amphotericinB cholesterylsulfate, amphotericinB lipid complex, ampicillin sodium, ampiroxicam, amrinone, amrubicin, amtolmetinguacil, anacetrapib, anagliptin, anagrelide, anamorelin, anastrozole, ancrod, androgen, andrographolide, anecortave, anidulafungin, aniracetam, anistreplase, anlotinib, antazoline, antiandrogens, antineoplaston A-10, antineoplaston AS2-1, antofloxacin hydrochloride, antroquinonol, apabetalone, apalutamide, apatinib mesylate, apaziquone, apilimod mesylate, apixaban, apomorphine, apomorphine hydrochloride, apremilast, aprepitant, apricitabine, aramchol, aranidipine, arasertaconazole, arasertaconazol enitrate, arbaclofen, arbaclofen placarbil, arbekacin, arbekacin sulfate, ardeparin sodium, arformoterol, argatroban, arhalofenate, arimoclomol, aripiprazole, aripiprazole lauroxil, armodafinil, arsenictrioxide, arsenious acid, artefenomel mesylate, artemether, artemotil, artenimol, arterolane maleate, artesunate, Artiss, asapiprant, asenapine, asimadoline, astodrimer, astragaloside, asunaprevir, ataciguat, ataluren, atazanavir, atazanavir sulfate, atenolol, atomoxetine, atorvastatin, atorvastatin calcium, atorvastatin strontium, atovaquone, atrasentan, atropine, auranofin, auriclosene, avacincaptadpegol sodium, avacopan, avanafil, avatrombopag, avibactam, avibactam sodium, AvidinOx, aviptadil, avitinib, avoralstat, axelopran, axitinib, azacitidine, azacytidine, azasetron, azelaicacid, azelastine, azelastine hydrochloride, azeliragon, azelnidipine, azilsartan, azilsartan medoxomil potassium, azilsartan trimethylethanolamine, azimilide, azithromycin, azithromycin lactobionate, aztreonam, aztreonam lysine, azvudine, baclofen, bafetinib, Baicalein, baicalin, BAK-freelatanoprost, balofloxacin, balsalazide, balsalazide sodium, bambuterol, barasertib, bardoxolone methyl, baricitinib, barnidipine, basmisanil, batefenterol succinate, bazedoxifene, beclabuvir, beclometasone dipropionate, beclomethasone dipropionate, bedaquiline, bedoradrine, belinostat, beloranib, belotecan, bempedoic acid, benapenem, benazepril, bencycloquidium bromide, bendamustine, bendamustine hydrochloride, benidipine, benserazide, bentamapimod, benzalkonium chloride, benzhydrocodone, benznidazole, benzocaine, benzoylperoxide, benzydamineHCL, bepotastine, bepotastine calciumdihydrate, bepotastine salicylate, beractant, beraprost sodium, besifloxacin, besifovir, besipirdine, beta-elemene, betahistine, betaine anhydrous, betamethasone, betamethasone butyrate propionate, betamethasonedipropionate, betamethasone valerate, betamipron, betaxolol, betaxolol hydrochloride, bethanechol, betrixaban, bevacizumab, bexagliflozin, bexarotene, bezafibrate, biafungin, biapenem, bicalutamide, bicizar, bictegravir, bicyclol, bilastine, bimatoprost, binimetinib, biotin, birabresibdihydrate, biskalcitrate potassium, bismuth subgallate, bismuthyl ecabet, bisnorcymserine, bisoprolol, bisoprolol fumarate, bitespiramycin, bixalomer, bleomycin, blonanserin, boanmycin hydrochloride, boceprevir, bortezomib, bosentan, bosentan hydrate, bosutinib, bovactant, brexpiprazole, briciclib sodium, brigatinib, brilacidin, brimapitide, brimonidine, brincidofovir, brinzolamide, brivanibalaninate, brivaracetam, brivudine, brolucizumab, bromazepam, bromfenac, bromfenac sodium, bromocriptine, bronchostat, brotizolam, bryostatin-1, bucindolol, bucladesine, budesonide, budipine, buflomedil, bulaquin, bunazosin, buparlisib, bupivacaine, bupivacaine hydrochloride, buprenorphine, buprenorphine hydrochloride, bupropion, bupropion hydrochloride, burixafor, buserelin acetate, buspirone, buspirone hydrochloride, busulfan, busulfex, butenafine, butorphanol tartrate, butylphthalide, cabazitaxel, cabergoline, cabotegravir, cabozantinib S-malate, cadazolid, cadrofloxacin, caffeine, caffeine citrate, cafnea, cafusertib hydrochloride, calcipotriol, calcitriol, calcium acetate, calciumfolinate, calcium levofolinate, calcium polycarbophil, calfactant, calmangafodipir, calsurf, camicinal, camostat mesylate, camptothecin, canagliflozin, candesartan, candesartan cilexetil, canfosfamide, cangrelor, cannabidiol, capecitabine, capmatinib, capsaicin, captopril, carbamazepine, carbetocin, carbidopa, carbinoxamine, carbocysteine, carboplatin, cardidopa, carfilzomib, carglumicacid, cariprazine, carisbamate, carmustine, carotegastmethyl, carteolol, carteolol hydrochloride, carumonam, carvedilol, carvedilolphosphate, caspofungin, catechin, cebranopadol, cediranib, cefaclor, cefadroxil, cefathiamidine, cefazolin sodium pentahydrate, cefcapene, cefdinir, cefditorenpivoxil, cefepime, cefepime dihydrochloride, cefetametpivoxil hydrochloride, cefiderocol, cefilavancin, cefminox, cefoperazone, cefoperazone sodium, cefoselis, cefotaxime, cefotaxime sodium, cefotiam, cefozopran, cefpirome, cefpodoxime, cefprozil, ceftaroline, ceftaroline fosamil, ceftazidime, ceftibuten, ceftobiprole medocaril, ceftolozane sulfate, ceftriaxone, ceftriaxone sodium, cefuroxime, cefuroxime sodium, celecoxib, celgosivir, celiprolol, cellprotect, cenestin, cenicriviroc, censavudine, centanafadine, cephalosporin, ceralifimod, cerdulatinib, ceritinib, ceriumnitrate, cetilistat, cetirizine, cetraxate, cevimeline, chenodeoxycholic acid, chlocibutamine, chlorhexidine, chlormadinone acetate, chlorogenicacid, chloroquine, chloroxoquinoline, chlorpheniramine, chlorpheniramine maleate, chlorpheniramine polistirex, chlortalidone, chlorthalidone, cholecalciferol, cholic acid, choline alfoscerate, choline diepalrestat, choline fenofibrate, ciclesonide, ciclopiroxolamine, ciclosporin, cidofovir, cidoxepin, cilastatin, cilazapril, cilnidipine, cilostazol, cimetidine, cinacalcet, cinepazide maleate, cinhyaluronate sodium, cinitapride tartrate, cipargamin, ciprofibrate, ciprofloxacin, ciprofloxacin hydrochloride, ciraparantag, circadin, cisatracurium besilate, cisplatin, citalopram, citalopram hydrobromide, citicoline, citrulline, cladribine, clarithromycin, clavulanate potassium, clavulanic acid, clazosentan, clevidipine, clevudine, clindamycin, clindamycin hydrochloride, clindamycin phosphate, clioquinol, clobazam, clobetasolpropionate, clobetasolpropionatefoam, clodronic acid, clofarabine, clofazimine, clomipramine, clomipramine hydrochloride, clonazepam, clonidine, clonidine hydrochloride, clopidogrel, clopidogrel besylate, clopidogrel bisulfate, clopidogrel camsylate, clopidogrel hydrogensulfate, clopidogrel napadisilate, clopidogrel resinate, clotrimazole, clozapine, cobamamide, cobicistat, cobimetinib, cobiprostone, codeine, codeine polistirex, colchicine, colecalciferol, colesevelam, colestilan, colforsin daropate, colfosceril palmitate, colistimethate sodium, conivaptan, copanlisib, copperhistidine, cortexolone 17alpha-propionate, cositecan, crenolanib, cridanimod sodium, crisaborole, crizotinib, crofelemer, crolibulin, cromoglicic acid, cromolyn sodium, cutamesine dihydrochloride, cyanocobalamin, cyclizine lactate, cyclobenzaprine hydrochloride, cyclophosphamide, cyclophosphamide monohydrate, cyclosporin, cyproterone, cyproterone acetate, cytarabine, cytarabine ocfosfate, dabigatran etexilate, dabrafenib, daclatasvir, dacomitinib, dalbavancin, dalcetrapib, dalfampridine, dalfopristin, dalteparin sodium, danaparoid sodium, danazol, danirixin, danoprevir, dantrolene sodium, danusertib, dapaconazole, dapagliflozin, dapagliflozin propanediol, dapiprazole, dapivirine, dapoxetine, daprodustat, dapsone, darifenacin, darinaparsin, darunavir, dasabuvir, dasatinib, dasotraline, daunorubicin, decitabine, decuprate, defactinib, deferasirox, deferiprone, deferoxamine mesylate, deflazacort, deflexifol, delafloxacin, delamanid, delapril, delapril hydrochloride, delavirdine, denibulin, deoxyandrographolide, dermatansulfate, desflurane, desipramine hydrochloride, desloratadine, desmopressin, desmopressin acetate, desogestrel, desonide, desvenlafaxine, deudextromethorphan hydrobromide, deuteporfin, deuterated levodopa, deuteratedvenlafaxine, deutetrabenazine, dexamethasone, dexamethasone acetate, dexamethasone cipecilate, dexamethasone palmitate, dexamethasone sodiumphosphate, dexamfetamine, dexanabinol, dexferrum, dexketoprofen trometamol, dexlansoprazole, dexmedetomidine, dexmethylphenidate, dexpramipexole, dexrazoxane, dexsotalol, dextroamphetamine saccharate, dextroamphetamine sulfate, dextromethorphan, dextromethorphan hydrobromide, dextropropoxyphene, diacerein, diamorphine hydrochloride, dianhydrogalactitol, diazepam, diazoxidecholine, diclofenac, diclofenac potassium, diclofenac sodium, diclofenamide, dicycloplatin, didanosine, dienogest, difluprednate, digoxin, dihomogamma-linolenic acid, dihydroergocristine, dihydroergotamine, dihydroergotamine mesylate, diltiazem, diltiazem hydrochloride, dimesna, dimethyl fumarate, dimiracetam, dinoprostone, diphenylcyclopropenone, dipraglurant, dipyridamole, diquafosoltetra sodium, dirithromycin, disufenton sodium, disulfiram, dithranol, d-methadone, docarpamine, docetaxel, dociparstat, docosanol, dofetilide, dolasetron, dolutegravir, domperidone, donafenib tosylate, donepezil, donepezil hydrochloride, dopamine, doravirine, doripenem, dorzolamide, dorzolamide hydrochloride, dosmalfate, doxacurium chloride, doxazosin, doxazosin mesylate, doxepin hydrochloride, doxercalciferol, doxifluridine, doxofylline, doxorubicin, doxorubicin hydrochloride, doxycycline, doxycycline hyclate, doxylamine succinate, dronabinol, dronedarone, drospirenone, droxidopa, D-tagatose, duloxetine, duloxetine hydrochloride, dutasteride, duvelisib, ebastine, eberconazole, ebselen, ecabet, econazolenitrate, ecopipam, edaravone, edivoxetine, edonerpic maleate, edoxaban, efatutazone, efavirenz, efinaconazole, eflornithine, efonidipin hydrochloride, egualen sodium, eicosapentaenoic acid monoglycerides, elafibranor, elagolix, elamipretide, elbasvir, eldecalcitol, eleclazine, elesclomol sodium, eletriptan, eliglustattartrate, elobixibat, eltrombopag, eluxadoline dihydrochloride, elvitegravir, emdogain, emedastine, emeramide, emixustat, emodepside, empagliflozin, emricasan, emtricitabine, enalapril, enalaprilmaleate, enasidenib, encenicline, enclomifene citrate, encorafenib, endoxifen, enobosarm, enoxacin gluconate, enoxaparin sodium, enprostil, entacapone, entasobulin, entecavir, entecavir maleate, entinostat, entospletinib, entrectinib, enzalutamide, enzastaurin, epacadostat, epalrestat, eperisone, epetraborole, ephedrine sulfate, epinastine hydrochloride, epinephrine, epirubicin, epirubicin hydrochloride, episalvan, epitinib, eplerenone, epoprostenol, epristeride, eprodisate, eprosartan, eptaplatin, eravacycline, erdafitinib, erdosteine, eribulin mesylate, erlotinib, ertapenem, erteberel, ertugliflozin, erythromycin, erythromycin acistrate, erythromycin stinoprate, escitalopram, esketamine, esketamine hydrochloride, eslicarbazepine acetate, esmolol hydrochloride, esomeprazole, esomeprazole magnesium, esomeprazole strontium, esomeprazole, estetrol, estradiol, estradiol acetate, estradiol cypionate, estradiol valerate, estrodiol, estrogen, esuberaprost sodium, eszopiclone, etamicastat, ethambutol hydrochloride, ethaselen, ethinylestradiol, ethylhydrogenfumarate calcium, ethylhydrogenfumarate magnesium, ethylhydrogenfumara tezinc, ethynylestradiol, etidronicacid, etimicin sulfate, etirinotecanpegol, etizolam, etodolac, etonogestrel, etoposide, etoposide phosphate, etoricoxib, etravirine, etripamil, eupatilin, evenamide hydrochloride, everolimus, evofosfamide, evogliptin, exemestane, exendin(9-39), exeporfinium chloride, ezatiostat, ezetimibe, ezutromid, fadolmidine, fadrozole, faldaprevir, falecalcitriol, famciclovir, famitinib, famotidine, fampridine, faropenem, fasitibant chloride, fasoracetam, fasudil, fasudil hydrochloride, fasudil mesylate, favipiravir, febarbamate, febuxostat, fedovapagon, felbamate, felbinac trometamol, felodipine, femitra, fenfluramine hydrochloride, fenobam, fenofibrate, fenofibric acid, fenoldopam, fenoterol, fenretinide, fentanyl, fentanyl citrate, fenticonazole, fermagate, ferriccitrate, ferricmaltol, ferumoxytol, fesoterodine fumarate, fevipiprant, fexinidazole, fexofenadine, fibrinsealant, fibrinogen, fibrinogensealant, fidaxomicin, filanesib, filgotinib, filociclovir, fimaporfin, fimasartan, finafloxacin, finafloxacin hydrochloride, finasteride, finerenone, fingolimod, fipamezole, firtecanpegol, flecainide, fleroxacin, flibanserin, flomoxef, floxuridine, fluazolepali, fluconazole, fludarabine, flumatinib, flumazenil, flunisolide, fluocinolone acetonide, fluocinonide, fluorapacin, fluorouracil, fluoxetine, fluoxetine hydrochloride, flupirtine, flurbiprofen, flurbiprofenaxetil, flurbiprofen sodium, flurithromycin, fluticasone, fluticasone furoate, fluticasone propionate, flutrimazole, fluvastatin, fluvoxamine, folic acid, folinate, foliumginkgo, fomepizole, fonadelpar, fondaparinux sodium, foretinib, formestane, formoterol, formoterol fumarate, forodesine, fosamprenavir, fosaprepitant, fosbretabulin, fosbretabulin disodium, fosfluconazole, fosfomycin, fosfomycindi sodium, fosfomycintrometamol, fosinopril, fosinopril sodium, fosmidomycin, fosphenytoin, fospropofol, fosravuconazole, fostamatinib, fostemsavir tromethamine, fotagliptin benzoate, fotemustine, frovatriptan, fruquintinib, fudosteine, fulvestrant, funapide, furosemide, fusidic acid, gabapentin, gabapentinenacarbil, gabexate mesylate, gacyclidine, gadobutrol, gadoversetamide, gadoxetate disodium, galantamine, galeterone, galidesivir, gallium nitrate, galunisertib, gambogic acid, ganaxolone, ganciclovir, ganetespib, ganirelix acetate, garenoxacin, gatifloxacin, gatifloxacin mesylate, gedatolisib, gefitinib, gemcabene, gemcitabine, gemcitabine hydrochloride, gemfibrozil, gemifloxacin, gemigliptin, gemigliptintartaric acid, genistein, gentamicin, gentiopicrin, gepirone, gepotidacin, gestodene, gestrinone, timolol maleate, gilteritinib, gimeracil, ginsenosideC-K, ginsenosideRg3, givinostat, glasdegib, glatiramer acetate, glecaprevir, glesatinib glycolate, glibenclamide, gliclazide, glimepiride, glipizide, glufosfamide, glutamine, glutathionarsenoxide, glycerol phenylbutyrate, glycopyrronium, glycopyrronium bromide, glycopyrronium tosylate, glycyrrhizi cacid, ganglioside, golotimod, gosogliptin, granisetron, granisetron hydrochloride, grazoprevir, guaifenesin, guaimesal, guanfacine, gusperimus trihydrochloride, haemophilusinfluenzae, halobetasol propionate, halofantrine, halometasone, healon, hematoporphyrin, hemearginate, hemocoagulase acutus, heparin, Herbiron, hetrombopag, hextend, higenaminehydrochloride, histamine dihydrochloride, HPPHphotosensitizer, humanapotransferrin, humanplasminogen, huperzineA, hyaluronate sodium, hydralazine, hydrochloride, hydrochlorothiazide, hydrocodone, hydrocodone bitartrate, hydrocodone polistirex, hydrocortisone, hydrogenperoxide, hydromorphone, hydromorphone hydrochloride, hydroxocobalamin, hydroxycarbamide, hydroxychloroquine, hydroxyprogesterone caproate, hydroxysafflor yellowA, hylastan, hypericin, hypoestoxide, ibandronate, ibandronic acid, iberogastN, ibodutant, ibrutinib, ibudilast, ibuprofen, ibutilide, ibutilide fumarate, icaritin, iclaprim, icosabutate, icosapent, icosapentethyl, icosapentethylester, icotinib hydrochloride, idalopirdine, idasanutlin, idebenone, idelalisib, idoxuridine, idronoxil, ifetroban, ifetrobansodium, iguratimod, ilansoprazole, ilaprazole, iloperidone, iloprost, iloprostbetadexclathrate, imatinib, imatinibmesylate, imeglimin, imidafenacin, imidapril, imidazole salicylate, imidol hydrochloride, imigliptin dihydrochloride, imipenem, imiquimod, imisopasem manganese, imrecoxib, incadronic acid, incobotulinumtoxin, indacaterol, indacaterol maleate, indapamide, indeloxazine, Indimitecan, indinavir, indisetron, indometacin, indoramin, indotecan, indoximod, inecalcitol, infigratinib, Ingaviring, ingenolmebutate, inhaled sodium nitrite, ferric carboxymaltose, inosine, intepirdine, iodiconazole, ipatasertib dihydrochloride, ipragliflozin, ipratropium, ipratropium bromide, iptakalim, irbesartan, irinotecan, irinotecan hydrochloride, irinotecan sucrosofate, irofulven, iron isomaltoside1000, iron protein succinylate, irosustat, irsogladine maleate, isavuconazonium chloride/sulfate, isodibut, isoflurane, isoniazid, isopropylunoprostone, isosorbidedi nitrate, isosorbide mononitrate, isosteviol, isothiafludine, isotretinoin, isradipine, istaroxime, istradefylline, itacitinib, itopride hydrochloride, itraconazole, ivabradine hemisulfate, ivabradine hydrochloride, ivacaftor, ivermectin, ivosidenib, aflibercept, ixabepilone, ixazomib citrate, kallikrein, kangbeide, ketamine, ketanserin, ketoconazole, ketoprofen, ketorolac, ketorolac tromethamine, ketotifen, kevetrin, kukoamine Bmesylate, L-4-chlorokynurenine, lacidipine, lacosamide, lactitol, ladarixin, ladostigil, laflunimus, lafutidine, lamivudine, lamotrigine, landiolol, landiolol hydrochloride, laninamivir octanoate, lanoconazole, lansoprazole, lanthanum carbonate, lapatinib, laquinimod, laromustine, lasmiditan, lasofoxifene, latanoprost, latanoprostenebunod, lauflumide, ledipasvir, lefamulin, leflunomide, lemborexant, lenalidomide, lentinan, lentinansulfate, lentinanviral, lenvatinib mesylate, lercanidipine, lesinurad, leteprinim, letermovir, letrozole, leucine, leuprorelin acetate, levalbuterol, levalbuterol hydrochloride, levamisole, levamlodipine, levamlodipine besylate, levamlodipine maleate, levetiracetam, levobupivacaine, levocabastine, levocabastine hydrochloride, levocarnitine, levocetirizine dihydrochloride, levodopa, levodoxazosin mesylate, levofloxacin, levoketoconazole, levomilnacipran, levonadifloxacin arginine salt, levonorgestrel, levonorgestrel butanoate, levo-phencynonate hydrochloride, levornidazole, levorphanol, levosimendan, levothyroxine sodium, levotuss, L-glutamine, lidocaine, lifitegrast, ligustrazine hydrochloride, limaprost, linagliptin, linezolid, liothyronine, liothyronine sodium, lipobean, liposomal curcumin, lipoteichoic acid, liranaftate, lisdexamfetamine, lisinopril, lisofylline, lisuridehydrogen maleate, lithiumcitrate, lithiumsuccinate, lixivaptan, lobaplatin, lobeglitazone, lodenafil carbonate, lofexidine, lomefloxacin, lomerizine, lomerizine dihydrochloride, lomitapide, lonafarnib, lonidamine, loperamide, loperamideoxide, lopinavir, loratadine, lorazepam, lorcaserin, lorediplon, lorlatinib, L-ornithineL-aspartate, lornoxicam, losartan, losartan potassium, losmapimod, loteprednoletabonate, lovastatin, loxapine, loxoprofen, L-praziquantel, lubiprostone, lucanthone, lucerastat, lucinactant, lucitanib hydrochloride, luliconazole, lumacaftor, lumateperone toluene sulfonate, lumefantrine, lumiracoxib, lunacalcipol, lurasidone, lurbinectedin, luseogliflozin hydrate, lusutrombopag, lysine acetylsalicylate, macimorelin, macitentan, mafenide, magnesium carbonate, magnesium isoglycyrrhizinate, mangafodipir, manidipine, manidipine dihydrochloride, mannitol, maraviroc, maribavir, marizomib, masilukast, masitinib, mavoglurant, maxacalcitol, mebendazole, mebiphon, mecamylamine, mecamylamine hydrochloride, mechlorethamine, mecobalamin, medroxyprogesterone, medroxyprogesteroneacetate, mefloquine, megestrol, megestrolacetate, meisuoshuli, melevodopa, meloxicam, melphalan, melphalanflufenamide hydrochloride, memantine, memantine hydrochloride, menadione sodium bisulfate, menatetrenone, mepacrine, mequinol, mercaptamine, mercaptamine bitartrate, mercaptamine hydrochloride, mercaptopurine, merestinib, meropenem, merotocin, mesalamine, mesalazine, metacavir, metadoxine, metamizolesodium, metaxalone, metergoline, metformin, metformin hydrochloride, methadone, methazolamide, methotrexate, methoxyflurane, methylaminolevulinate hydrochloride, methylnaltrexone bromide, methylnaltrexone, methylphenidate, methylphenidate hydrochloride, methylprednisolone, methylprednisolone aceponate, methylthioninium chloride, metirosine, metoclopramide, metoprolol, metoprolol succinate, metrifonate, metronidazole, metyrapone, mexiletine, mibefradil, miconazole, miconazole nitrate, midazolam, midazolam hydrochloride, midodrine, midostaurin, mifamurtide, mifepristone, migalastat, miglitol, miglustat, milnacipran, milrinone, miltefosine, minaprine, minocycline, minocycline hydrochloride, minodronic acid, minoxidil, mirabegron, miriplatin hydrate, mirodenafil, mirodenafil hydrochloride, mirogabalin, mirtazapine, misoprostol, mitiglinide, mitomycin, mitoxantrone, mitoxantrone hydrochloride, mivotilate, mizolastine, mizoribine, mocetinostat dihydrobromide, moclobemide, modafinil, doxycycline, modipafant, moexipril, mofezolac, molidustat, molindone hydrochloride, momelotinib, mometasone, monepantel, monoammonium glycyrrhizinate, monobenzone, monosodium alphaluminol, monoterpene perillyl alcohol, montelukast, montelukast sodium, montmorillonite, moracizine, morinidazole, morphine, morphine glucuronide, morphine pitavastatin, morphine sulfate, morphothiadine mesilate, mosapride, motolimod, moxidectin, moxifloxacin, moxifloxacin hydochloride, moxonidine, moxonidine hydrochloride, mozavaptan, muparfostat sodium, mupirocin, mycobactovir, mycophenolatemofetil, myristylnicotinate, nabilone, nabiximols, nabumetone, N-acetylcysteine, nacystelyn, nadifloxacin, nadolol, nadroparin calcium, naftifine hydrochloride, naftopidil, nalbuphine, nalbuphine sebacate, naldemedine, nalfurafine, nalmefene, naloxegol, naloxone, naloxone hydrochloride, naltrexone, naltrexone hydrochloride, naluzotan, nandrolone decanoate, napabucasin, naphazoline, naphthoquine, naproxen, naproxen sodium, naquotinib mesylate, naratriptan, narlaprevir, nasapaque, nasaruplase, nastorazepide calcium, nateglinide, navamepent, nazartinib, nebivolol, necuparanib, nedaplatin, nedocromil, nelarabine, nelfinavir, nelotanserin, nemonapride, nemonoxacin, neoandrographolide, neosaxitoxin, neostigmine methyl sulfate, nepadutant, nepafenac, nepicastat, nepolong, neramexane, neratinib, neridronic acid, netarsudil, netilmicin, netupitant, nevirapine, niacin, nicardipine, nicergoline, nicorandil, nicotiflorin, nicotine, nicotinicacid, nicousamide, nifedipine, nifekalant, nifeviroc, Nifurtimox, nifurzide, nikkomycin, nilotinib, nilutamide, nilvadipine, nimesulide, nimodipine, nimorazole, ningetinib, nintedanib, niraparib, nisoldipine, nitazoxanide, nitisinone, nitrendipine, nitricoxide, nitroglycerin, nitroglycerine, nizatidine, nokxaban, nolatrexed, nomegestrol acetate, norelgestromin, norepinephrine, norethindrone, norethindrone acetate, norethindrone enantate, norethisterone, norethisterone acetate, norfloxacin, norgestimate, noribogaine, norursodeoxycholic acid, obeticholicacid, octenidine, octohydroaminoacridine succinate, octreotide, octreotide hydrochloride, odalasvir, odanacatib, odiparcil, ofloxacin, olanzapine, olaparib, olesoxime, oliceridine, olmesartan, olmesartan cilexetil, olmesartan medoxomil, olodaterol, olodaterol hydrochloride, olopatadine, olopatadine hydrochloride, olprinone, olsalazine, oltipraz, omacetaxine mepesuccinate, omadacycline, omarigliptin, omaveloxolone, ombitasvir, omecamtivmecarbil, omega-3 carboxylicacids, omeprazole, omigapil, omoconazole, onalespib, onapristone, ondansetron, ondelopran, opicapone, opipramol, methylphenidate, orcinoside, orilotimod, oritavancin, orlistat, ornithine phenylacetate, ornoprostil, ortataxel, orteronel, orthovisc, orvepitant, oseltamivir, osilodrostat, osimertinib, Osiris Phleum pratense, ospemifene, oteracil potassium, oteseconazole, oxaliplatin, oxaloacetic acid, oxandrolone, oxazepam, oxcarbazepine, oxfendazole, oxidizedglutathione sodium, oxiracetam, oxybutynin, oxybutynin hydrochloride, oxycodone, oxycodone hydrochloride, oxymetazoline, oxymetazoline hydrochloride, oxymorphone, oxytocin, ozagrel, ozagrel hydrochloride, ozagrelsodium, ozanimod, ozenoxacin, paclitaxel, paclitaxel poliglumex, pacritinib, palbociclib, paliperidone, paliperidone palmitate, palmidrol, palonosetron, palovarotene, pamidronate disodium, pancrelipase, panipenem, panobinostat, pantoprazole, paracetamol, parecoxib, paricalcitol, paritaprevir, parnaparin sodium, parogrelil, paromomycin, paroxetine, paroxetine hydrochloride hemihydrate, paroxetine mesylate, patiromer calcium, patupilone, pazopanib, pazufloxacin, pazufloxacin mesylate, pefcalcitol, peficitinib, pegylatedapo-filgrastim, pelubiprofen, pemafibrate, pemetrexed disodium, pemirolast, pemirolast potassium, pemirolast sodium, penciclovir, penehyclidine hydrochloride, pentamidine, pentetate calcium trisodium, pentetatezinc trisodium, pentetrazol, pentosan polysulfate sodium, pentostatin, pentoxifylline, peramivir, perampanel, perchlozone, peretinoin, perflenapent, perflubronemulsion, perfluorooctyl bromide, pergolide, perhexiline maleate, perifosine, perindopril, perindopril arginine, perospirone, pevonedistat, pexidartinib, PhagoBioDerm, phenchlobenpyrrone, phenethyl isothiocyanate, phenoxybenzamine hydrochloride, phentermine, phentermine hydrochloride, phentolamine mesylate, phenylbutyrate, phenylephrine, phenylephrine hydrochloride, phenytoin, phosphazid, pibrentasvir, picibanil, picroliv, picropodophyllin, pidotimod, pilocarpine, pilocarpine hydrochloride, pilsicainide, pimasertib hydrochloride, pimavanserin, pimecrolimus, pimobendan, pinocembrin, pinometostat, pioglitazone, pioglitazone hydrochloride, pipamperone, pipecuronium, piperacillin, piperacillin sodium, piperaquine, piperaquine phosphate, piperidone hydrochloridum, piperine, piperphentonamine, piracetam, pirarubicin, pirfenidone, pirmenol, piromelatine, pirotinib, piroxicam, piroxicambetadex, pitavastatin, pitavastatin calcium, pitolisant, pixantrone, plazomicin, pleconaril, plerixafor, plinabulin, pocapavir, hydromorphone, podofilox, polaprezinc, polmacoxib, polydatin, polyoxidonium, pomaglumetad methionil, pomalidomide, ponatinib, ponesimod, porfimer sodium, posaconazole, posiphen, potassium bicarbonate, potassium citrate, potassium clavulanate, poziotinib, pracinostat, pradefovir, pralatrexate, pramipexole, pramiracetam, pranlukast, pranlukast hydrate, prasterone, prasugrel, pravastatin, prazosin, prednimustine, prednisolone, prednisoloneacetate, prednisolone sodiumphosphate, prednisone, pregabalin, prempro, presatovir, pretomanid, previdersin, prexasertib, pridopidine, prilocaine, pritelivir, procaterol hydrochloride, prochlorperazine, prochlorperazinemaleate, profezyme, progesterone, progestogen, progestogendienogest, proguanil, promethazine, promitil, propafenone, propagermanium, propofol, propranolol, propranolol hydrochloride, prostat, proxodolol, prucalopride, prulifloxacin, prurisol, prussianblueinsoluble, pseudoephedrine, pseudoephedrine hydrochloride, puerarin, puquitinib mesylate, pyrazinamide, pyridoxamine dihydrochloride, pyridoxine hydrochloride, pyrimethamine, pyronaridine, pyrroltinibmaleate, quazepam, quetiapine fumarate, quetiapine, quinagolide hydrochloride, quinapril hydrochloride, quinidine sulfate, quinine sulfate, quinupristin, quisinostat, quizartinibdi hydrochloride, rabeprazole, rabeprazolesodium, rabeximod, racecadotril, radezolid, radotinib, ralfinamide, ralimetinib, ralinepag, raloxifene, raltegravir, raltitrexed, ramatroban, ramelteon, ramipril, ramosetron, ranitidine, ranitidine bismuth citrate, ranolazine, rasagiline, ravidasvir hydrochloride, raxatrigine, rebamipide, rebastinib, reboxetine, reboxetine mesylate, recilisib sodium, recoflavone, redaporfin, ibuprofen, naproxen, glycopyrronium bromide, refametinib, regorafenib, relebactam, relenopride, relugolix, remeglurant, remifentanil, remifentanil hydrochloride, remimazolam, remimazolam tosylate, remogliflozin etabonate, repaglinide, reparixin, repirinast, amlexanox, chlorcyclizine hydrochloride, bucillamine, guanabenz, mazindol, naltrexone, nitisinone, ondansetron, phacetoperane, retigabine, rosiglitazone, sodium phenylbutyrate, resiniferatoxin, resiquimod, resminostat, resveratrol, retagliptin, retapamulin, retigabine, retinoicacid, retosiban, revaprazan, revefenacin, reviparin sodium, rhein, rhenium-186 etidronate, ribavirin, ribociclib, ricolinostat, ridinilazole, ridostin, rifabutin, rifampicin, rifamycin, rifapentine, rifaximin, rigosertib sodium, rilapladib, rilpivirine, rilpivirine hydrochloride, riluzole, rimantadine, rimeporide, rimexolone, riociguat, ripasudil hydrochloride hydrate, risedronate sodium, risperidone, ritonavir, rivaroxaban, rivastigmine, rivipansel sodium, rizatriptan, rizatriptan benzoate, rmulation, rociletinib, roflumilast, rokitamycin, rolapitant, romurtide, ronacaleret, roneparstat, ronopterin, ropinirole, ropinirole hydrochloride, ropivacaine, rosebengal sodium, rosiglitazone, rosiglitazone maleate, rosiglitazone sodium, rostafuroxin, rosuvastatin, rosuvastatin calcium, rotigotine, rovatirelin, roxadustat, roxithromycin, rubitecan, rucaparib phosphate, rufinamide, rufloxacin, rupatadine, ruxolitinib, S-(-)-ornidazole phosphate disodium, sabarubicin, sacubitril, safinamide, salbutamol, salbutamol sulfate, salicyclic acid, salmeterol, salmeterol xinafoate, salubrinal, salvicine, samarium(153Sm) lexidronam, samidorphan, S-amlodipine nicotinate, sapacitabine, sapropterin, sapropterin dihydrochloride, saquinavir, saracatinib, sarecycline, saroglitazar, sarpogrelate hydrochloride, savolitinib, saxagliptin, scopolamine, scorpionvenom, omega-3polyunsaturated fatty acid, secnidazole, segesterone acetate, selegiline, selegiline hydrochloride, selepressin, selexipag, seliciclib, selinexor, selisistat, selumetinib, selurampanel, sepranolone, seratrodast, serlopitant, sertaconazole, sertaconazole nitrate, sertindole, sertraline, sertraline hydrochloride, setipiprant, sevelamer carbonate, sevelamer hydrochloride, seviteronel, sevoflurane, sevuparin sodium, sibutramine maleate, sibutramine mesylate, sildenafil, sildenafil citrate, silibinin dihydrogen succinate, silmitasertib, silodosin, silver sulfadiazine, simeprevir, simmitecan hydrochloride, simotinib hydrochloride, simvastatin, sinotecan, siponimod, sirolimus, sitafloxacin, sitagliptin, sitagliptinphosphate, sivelestat, sizofiran, smilagenin, S-modafinil, sobuzoxane, sodium aescinate, sodium ascorbate, sodium benzoate, sodium bicarbonate, sodium chromoglycate, sodium ferricgluconate complex, sodium glycididazole, sodium gualenate, sodium hyaluronate, sodium ibandronate, sodium nitrate, sodium nitrite, sodium oxybate, sodium phenylacetate, sodium phenylbutyrate, sodium polysulthionate, sodium prasteronesulfate, sodium pyruvate, sodium taurocholate, sodium thiosulfate, sodium zirconiumcyclosilicate, sofosbuvir, sofpironium bromide, solabegron, solifenacin, solithromycin, sonidegib, sonolisib, sophocarpine, sophoridine hydrochloride, sorafenib, sorbitol, sotagliflozin, sotirimod, sotrastaurin, sotylize, sovaprevir, sparfloxacin, sparsentan, spebrutinib, spirapril, spironolactone, squalamine, stannsoporfin, stavudine, S-tenatoprazole, stepronin, stiripentol, streptozocin, strontium malonate, strontium ranelate, succinic acid, sucralfate, sucroferric oxyhydroxide, sufentanil, suftalanzinc, sugammadex, sulbactam, sulbactam sodium, sulcardine sulfate, sulfamethoxypyrazine, sulfasalazine, sulfatinib, sulfonylurea, sulforaphane, sulfotanshinone sodium, sulindac, sulodexide, sulphamethoxazole, sulthiame, sumatriptan, sumatriptan succinate, sunitinib, sunstone, suplasyn, suplatast tosilate, suramin sodium, verapamil hydrochloride, rilpivirine, sutezolid, suvorexant, tacalcitol, tacrine, tacrolimus, tadalafil, tafamidis, tafenoquine, tafluprost, tafoxiparin sodium, taladegib, talaporfin, talazoparib, talipexole, taltirelin, tamibarotene, tamoxifen, tamsulosin, tamsulosin hydrochloride, tandospirone, tanespimycin, tapentadol, tarafenacin, tarenflurbil, tarloxotinib bromide, taselisib, tasimelteon, tasquinimod, tavaborole, tavilermide, tazarotene, tazemetostat, tazobactam, tazobactam sodium, tebipenem pivoxil, tecarfarin, tecovirimat, tectorigenin sodiumsulfonate, tedisamil, tedizolid phosphate, tefinostat, tegafur, tegaserod, teicoplanin, telaprevir, telapristone acetate, telatinib, telbivudine, telithromycin, telmisartan, telotristatetiprate, temanogrel, temocapril, temoporfin, temozolomide, temsirolimus, tenalisib, tenapanor, teneligliptin, tenofovir, tenofoviralafenamide, tenofovirdipivoxil fumarate, tenofovir disoproxil aspartate, tenofovir disoproxil fumarate, tenoxicam, tepotinib, teprenone, terameprocol, terazosin, terbinafine, terbinafine hydrochloride, terguride, teriflunomide, tesevatinib, tesofensine, testosterone, testosterone undecanoate, tetrabenazine, tetracaine, tetracaine hydrochloride, tetrahydrocannabidiol, tetrathiomolybdate, tetryzoline, tezacaftor, thalidomide, theliatinib, theophylline, therapeutic, thiazide, thienorphine hydrochloride, thiotepa, thrombin, thromboreductin, thyroxine, tiagabine, tianeptine, tibolone, ticagrelor, ticlopidine, tigecycline, tiludronatedi sodium, timolol, timolol maleate, tindamax, tinidazole, tinzaparin sodium, tioconazole, tiopronin, tiotropium bromide, tiotropium bromide monohydrate, tipelukast, tipepidine hibenzate, tipifarnib, tipiracil hydrochloride, tipranavir, tirapazamine, tirasemtiv, tirilazad, tirofiban, tirofiban hydrochloride, tivantinib, tivozanib, tizanidine, tobramycin, tocofersolan, tocoretinate, tofacitinib, tofogliflozin, tolcapone, tolimidone, tolperisone, tolterodine, tolterodine tartrate, tolvaptan, tonabersat, topiramate, topiroxostat, topotecan, topotecan hydrochloride, torasemide, toreforant, toremifene, tosedostat, tosufloxacin, totrombopag, tozadenant, trabectedin, trabodenoson, tradipitant, tramadol, tramadol hydrochloride, trametinib, trandolapril, tranexamic acid, tranilast, transcrocetinate-sodium, transepithelial riboflavin, trantinterol hydrochloride, travoprost, trazodone, trehalose, trelagliptin succinate, treosulfan, treprostinil, treprostinil diolamine, tretinoin, triamcinolone acetonide, triapine, triazolam, tribendimidine, trichlormethiazide, triciribine, triclabendazole, triclocarban, trientine hydrochloride, trifarotene, trifluridine, triflusal, triheptanoin, trilostane, trimebutine3-thiocarbamoyl-benzenesulfonate, trimebutine tosylate, trimegestone, trimethoprim, trimetrexate, trinitrate, tripotassium dicitratobismuthate, trofinetide, tropicamide, tropisetron, trospiumchloride, trovafloxacin, troxipide, tucatinib, tulobuterol, tylerdipinehydrochloride, ubenimex, ubidecarenone, ubrogepant, udenafil, ulinastatin, ulipristal, ulixertinib, ulobetasol, umeclidinium, umeclidinium bromide, upamostat, uprosertib, uracil, urapidil, uridinetriacetate, uroacitides, ursodeoxycholic acid, ursolicacid, vaborbactam, vadadustat, valaciclovir, valaciclovir hydrochloride, valbenazine, valdecoxib, valganciclovir, valomaciclovir stearate, valproic acid, valrubicin, valsartan, valsartan trisodium hemipentahydrate, vancomycin, vancomycin hydrochloride, vandetanib, vaniprevir, vanoxerine, vapendavir, vardenafil hydrochloride, varenicline, varithena, varlitinib, vatiquinone, vavelta, veliparib, velpatasvir, velusetrag, vemurafenib, venetoclax, venlafaxine, venlafaxine hydrochloride, vepoloxamer, verapamil, verapamil hydrochloride, verdinexor, veregen, vericiguat, verinurad, vernakalant, vernakalant hydrochloride, verosudil, verteporfin, verubecestat, verubulin, vesatolimod, vesnarinone, vibegron, vicagrel, vigabatrin, vilanterol, vilanterol trifenatate, vilaprisan, vilazodone, vildagliptin, vincristine sulfate, vinflunine, vinorelbine, vinpocetine, vintafolide, viralym-C, vismodegib, vistusertib, vitamin E nicotinicate, vizomitin, voglibose, volasertib, volixibat potassium ethanolate hydrate, vonoprazan fumarate, vorapaxar, voriconazole, vorinostat, vortioxetine, vortioxetine hydrobromide, vosaroxin, voxilaprevir, warfarin, xemilofiban, yimitasvir, yonkenafil, zabofloxacin, zafirlukast, zalcitabine, zaleplon, zaltoprofen, zamicastat, zanamivir, zemiStatin, Z-endoxifen hydrochloride, zibotentan, zidebactam, zidovudine, zileuton, zincacetate, zinostatin stimalamer, ziprasidone, zofenopril, zogenix, zoledronate D,L-lysinemonohydrate, zoledronate disodium, zoledronic acid, zoliflodacin, zolmitriptan, zolpidem, zolpidem tartrate, zonisamide, zopiclone, zotepine, zucapsaicin, zuclopenthixol, and zuretinol acetate.

In certain embodiments, traditional Chinese medicine is selected from the group consisting of Abelmoschi Corolla, Abri Herba, Abutili Semen, Acanthopanacis Cortex Acanthopanacis Senticosi Radix Et Rhizoma Seu Caulis, Acanthopanax Extract, Achilleae Herba, Achyranthis Bidentatae Radix, Aconiti Kusnezoffii Folium, Aconiti Kusnezoffii Radix Cocta, Aconiti Kusnezoffii Radix, Aconiti Lateralis Radix Praeparata, Aconiti Radix Cocta, Aconiti Radix, Acori Calami Rhizoma, Acori Tatarinowii Rhizoma, Adenophorae Radix, Aesculi Semen, Agkistrodon, Agrimoniae Herba, Ailanthi Cortex, Ajugae Herba, Akebiae Caulis, Akebiae Fructus, Albiziae Cortex, Albiziae Flos, Alismatis Rhizoma, Allii Macrostemonis Bulbus, Allii Sativi Bulbus, Allii Tuberosi Semen, Aloe, Alpiniae Katsumadai Semen, Alpiniae Officinarum Rhizoma, Alpiniae Oxyphyllae Fructus, Alumen, Amomi Fructus Rotundus, Amomi Fructus, Ampelopsis Radix, Andrographis Herba, Andrographolides, Anemarrhenae Rhizoma, Anemones Raddeanae Rhizoma, Angelicae Dahuricae Radix, Angelicae Pubescentis Radix, Angelicae Sinensis Radix, Anisi Stellati Fructus, Apocyni Veneti Folium, Aquilariae Lignum Resinatum, Arcae Concha, Arctii Fructus, Ardisiae Crenatae Radix, Ardisiae Japonicae Herba, Arecae Pericarpium, Arecae Semen Tostum, Arecae Semen, Arisaema Cum Bil, Arisaematis Rhizoma Preparatum, Arisaematis Rhizoma, Aristolochiae Fructus, Aristolochiae Herba, Armeniacae Semen Amarum, Arnebiae Radix, Artemisiae Annuae Herba, Artemisiae Argyi Folium, Artemisiae Scopariae Herba, Asari Radix Et Rhizoma, Asiatic Moonseed Root Extract, Asini Corii Colla, Asparagi Radix, Aspongopus, Asteris Radix Et Rhizoma, Astragali Complanati Semen, Astragali Radix Praeparata Cum Melle, Astragali Radix, Atractylodis Macrocephalae Rhizoma, Atractylodis Rhizoma, Aucklandiae Radix, Aurantii Fructus Immaturus, Aurantii Fructus, Bambusae Caulis In Taenias, Bambusae Concretio Silicea, Baphicacanthis Cusiae Rhizoma Et Radix, Belamcandae Rhizoma, Belladonna Extract, Belladonna Liquid Extract, Belladonnae Herba, Benincasae Exocarpium, Benzoinum, Berberidis Radix, Bergeniae Rhizoma, Bergenin, Bistortae Rhizoma, Bletillae Rhizoma, Bolbostemmatis Rhizoma, Bombyx Batryticatus, Borneolum Syntheticum, Borneolum, Bovis Calculus Artifactus, Bovis Calculus Sativus, Bovis Calculus, Breviscapine, Broussonetiae Fructus, Bruceae Fructus, Bubali Cornu, Buddlejae Flos, Bufonis Venenum, Bungarus Parvus, Bupleuri Radix, Calamina, Callicarpae Caulis Et Foliium, Callicarpae Formosanae Folium, Callicarpae Macrophyllae Folium, Calomelas, Campsis Flos, Canarii Fructus, Canavaliae Semen, Cannabis Fructus, Capsici Fructus, Carotae Fructus, Carpesii Fructus, Carthami Flos, Caryophylli Flos, Caryophylli Fructus, Cassiae Semen, Castor Oil, Catechu, Celosiae Cristatae Flos, Celosiae Semen, Centella Total Glucosides, Centellae Herba, Centipedae Herba, Cera Chinensis, Cera Flava, Cervi Cornu Degelatinatum, Cervi Cornu Pantotrichum, Cervi Cornu, Cervi Cornus Colla, Chaenomelis Fructus, Changii Radix, Chebulae Fructus Immaturus, Chebulae Fructus, Chelidonii Herba, Chinese Angelica Liquid Extract, Chloriti Lapis, Choerospondiatis Fructus, Chrysanthemi Flos, Chrysanthemi Indici Flos, Chuanxiong Rhizoma, Cibotii Rhizoma, Cicadae Periostracum, Cichorii Herba, Cichorii Radix, Cimicifugae Rhizoma, Cinnabaris, Cinnamomi Cortex, Cinnamomi Ramulus, Cinnamon Oil, Cirsii Herba, Cirsii Japonici Herba Carbonisata, Cirsii Japonici Herba, Cissampelotis Herba, Cistanches Herba, Citri Exocarpium Rubrum, Citri Fructus, Citri Grandis Exocarpium, Citri Reticulatae Pericarpium Viride, Citri Reticulatae Pericarpium, Citri Reticulatae Semen, Citri Sarcodactylis Fructus, Clematidis Armandii Caulis, Clematidis Radix Et Rhizoma, Clinopodii Herba, Cnidii Fructus, Codonopsis Radix, Coicis Semen, Commelinae Herba, Conyzae Herba, Coptidis Rhizoma, Cordyceps, Corni Fructus, Corydalis Bungeanae Herba, Corydalis Decumbentis Rhizoma, Corydalis Rhizoma, Crataegi Folium, Crataegi Fructus, Cremastrae Pseudobulbus, Pleiones Pseudobulbus, Crinis Carbonisatus, Croci Stigma, Crotonis Fructus, Crotonis Semen Pulveratum, Curculiginis Rhizoma, Curcumae Longae Rhizoma, Curcumae Radix, Curcumae Rhizoma, Cuscutae Semen, Cyathulae Radix, Cyclovirobuxine, Cynanchi Atrati Radix Et Rhizoma, Cynanchi Paniculati Radix Et Rhizoma, Cynanchi Stauntonii Rhizoma Et Radix, Cynomorii Herba, Cyperi Rhizoma, Dahurian Rhododendron Leaf Oil, Dalbergiae Odoriferae Lignum, Daturae Flos, Dendrobii Caulis, Dendrobii Officinalis Caulis, Descurainiae Semenlepidii Semen, Desmodii Styracifolii Herba, Dianthi Herba, Dichroae Radix, Dictamni Cortex, Dioscorea Panthaicae Rhizoma, Dioscoreae Hypoglaucae Rhizoma, Dioscoreae Nipponicae Rhizoma, Dioscoreae Rhizoma, Dioscoreae Spongiosae Rhizoma, Dipsaci Radix, Draconis Sanguis, Drynariae Rhizoma, Dryopteridis Crassirhizomatis Rhizoma Carbonisatum, Dryopteridis Crassirhizomatis Rhizoma, Echinopsis Radix, Ecliptae Herba, Entadae Semen, Entianae Rhodanthae Herba, Ephedrae Herba, Ephedrae Radix Et Rhizoma, Epimedii Folium, Epimedii Wushanensis Folium, Equiseti Hiemalis Herba, Erigerontis Herba, Eriobotryae Folium, Eriocauli Flos, Erodii Herba Geranii Herba, Erycibes Caulis, Eucalyptus Oil, Eucommiae Cortex, Eucommiae Folium, Euodiae Fructus, Eupatorii Herba, Eupatorii Lindleyani Herba, Euphorbiae Ebracteolatae Radix, Euphorbiae Hirtae Herba, Euphorbiae Humifusae Herba, Euphorbiae Pekinensis Radix, Euphorbiae Semen Pulveratum, Euphorbiae Semen, Eupolyphaga Steleophaga, Euryales Semen, Fagopyri Dibotryis Rhizoma, Farfarae Flos, Ferulae Resina, Fibraureae Caulis, Fibriuretinin, Fluoritum, Foeniculi Fructus, Forsythiae Fructus, Fraxini Cortex, Fritillariae Cirrhosae Bulbus, Fritillariae Hupehensis Bulbus, Fritillariae Pallidiflorae Bulbus, Fritillariae Thunbergii Bulbus, Fritillariae Ussuriensis Bulbus, Galangae Fructus, Galla Chinensis, Galli Gigerii Endothelium Corneum, Ganoderma, Capillary Wormwood Extract, GardeniaeFructus Praeparatus, Gardeniae Fructus, Gastrodiae Rhizoma, Gecko, Gei Herba, Gendarussae Herba, Genkwa Flos, Gentianae Macrophyllae Radix, Gentianae Radix Et Rhizoma, Ginger Liquid Extract, Ginkgo Folium, Ginkgo Leaves Extract, Ginkgo Semen, Ginseng Folium, Ginseng Radix Et Rhizoma Rubra, Ginseng Radix Et Rhizoma, Glabrous Sarcandra Extract, Glechomae Herba, Gleditsiae Fructus Abnormalis, Gleditsiae Sinensis Fructus, Gleditsiae Spina, Glehniae Radix, Glycyrrhizae Radix Et Rhizoma Praeparata Cum Melle, Glycyrrhizae Radix Et Rhizoma, Gossampini Flos, Granati Pericarpium, Gypsum Fibrosum, Gypsum Ustum, Haematitum, Haliotidis Concha, Halitum, Halloysitum Rubrum, Hawthorn Leave Extract, Hedysari Radix Praeparata Cum Melle, Hedysari Radix, Hibisci Mutabilis Folium, Hippocampus, Hippophae Fructus, Hirudo, Homalomenae Rhizoma, Hordei Fructus Germinatus, Houttuyniae Herba, Hydrargyri Oxydum Rubrum, Hyoscyami Semen, Hyperici Perforati Herba, Ilicis Chinensis Folium, Ilicis Cornutae Folium, Ilicis Rotundae Cortex, Ulicii Cortex, Impatientis Semen, Imperatae Rhizoma, Indigo Naturalis, Inulae Flos, Inulae Herba, Inulae Radix, Iridis Tectori Rhizoma, Isatidis Folium, Isatidis Radix, Juglandis Semen, Jujubae Fructus, Junci Medulla, Kadsurae Caulis, Kaempferiae Rhizoma, Kaki Calyx, Kansui Radix, Knoxiae Radix, Kochiae Fructus, Lablab Semen Album, Laggerae Herba, Lagotidis Herba, Laminariae Thallus Eckloniae Thallus, Lamiophlomis Herba, Lasiosphaera Calvatia, Leonuri Fructus, Leonuri Herba, Leonurus Liquid Extract, Licorice Extract, Licorice Liquid Extract, Ligustici Rhizoma Et Radix, Ligustri Lucidi Fructus, Lilii Bulbus, Limonitum, Linderae Radix, Lini Semen, Liquidambaris Fructus, Liquidambaris Resina, Liriopes Radix, Litchi Semen, Litseae Fructus, Lobeliae Chinensis Herba, Longan Arillus, Lonicerae Flos, Lonicerae Japonicae Caulis, Lonicerae Japonicae Flos, Lophatheri Herba, Luffae Fructus Retinervus, Lycii Cortex, Lycii Fructus, Lycopi Herba, Lycopodii Herba, Lygodii Spora, Lysimachiae Herba, Lysionoti Herba, /-Borneolum, /-Menthol, Magnetitum, Magnoliae Flos, Magnoliae Officinalis Cortex, Magnoliae Officinalis Flos, Mahoniae Caulis, Malvae Fructus, Manis Squama, Mantidis OOTheca, Margarita, Margaritifera Concha, Marsdeniae Tenacissimae Caulis, Mel, Melanteritum, Meliae Cortex, Melo Semen, Menispermi Rhizoma, Menthae Haplocalycis Herba, Meretricis Concha, Cyclinae Concha, Micae Lapis Aureus, Microctis Folium, Mirabilitum Praeparatum, Momordicae Semen, Mori Cortex, Mori Folium, Mori Fructus, Mori Ramulus, Morindae Officinalis Radix, Moschus, Moslae Herba, Moutan Cortex, Mume Flos, Mume Fructus, Murrayae Folium Et Cacumen, Mylabris, Myristicae Semen, Myrrha, Nardostachyos Radix Et Rhizoma, Natrii Sulfas Exsiccatus, Natrii Sulfas, Nelumbinis Folium, Nelumbinis Plumula, Nelumbinis Receptaculum, Nelumbinis Rhizomatis Nodus, Nelumbinis Semen, Nelumbinis Stamen, Nigellae Semen, Notoginseng Radix Et Rhizoma, Notoginseng Total Saponins, Notoginseng Triol Saponins, Notopterygii Rhizoma Et Radix, Ocimum Gratissimum Oil, Olibanum, Omphalia, Ophicalcitum, Ophiopogonis Radix, Orostachyis Fimbriatae Herba, Oroxyli Semen, Oryzae Fructus Germinatus, Osmundae Rhizoma, Ostreae Concha, Paeoniae Radix Alba, Paeoniae Radix Rubra, Panacis Japonici Rhizoma, Panacis Majoris Rhizoma, Panacis Quinquefolii Radix, Papaveris Pericarpium SI, Paridis Rhizoma, Patchouli Oil, Pegaeophyti Radix Et Rhizoma, Peppermint Oil, Perillae Caulis, Perillae Folium, Perillae Fructus, Periplocae Cortex, Persicae Ramulus, Persicae Semen, Peucedani Decursivi Radix, Peucedani Radix, Pharbitidis Semen, Phellodendri Amurensis Cortex, Phellodendri Chinensis Cortex, Pheretima, Phragmitis Rhizoma, Phyllanthi Fructus, Physalis Calyx Seu Fructus, Physochlainae Radix, Phytolaccae Radix, Picrasmae Ramulus Et Folium, Picriae Herba, Picrorhizae Rhizoma, Pinelliae Rhizoma Praeparatum Cum Alumine, Pinelliae Rhizoma Praeparatum Cum Zingibere Et Alumine, Pinelliae Rhizoma Praeparatum, Pinelliae Rhizoma, Pini Lignum Nodi, Pini Pollen, Piperis Fructus, Piperis Kadsurae Caulis, Piperis Longi Fructus, Plantaginis Herba, Plantaginis Semen, Platycladi Cacumen, Platycladi Semen, Platycodonis Radix, Pogostemonis Herba, Polygala Liquid Extract, Polygalae Japonicae Herba, Polygalae Radix, Polygonati Odorati Rhizoma, Polygonati Rhizoma, Polygoni Avicularis Herba, Polygoni Cuspidati Rhizoma Et Radix, Polygoni Multiflori Caulis, Polygoni Multiflori Radix Praeparata, Polygoni Multiflori Radix, Polygoni Orientalis Fructus, Polygoni Perfoliati Herba, Polygoni Tinctorii Folium, Polyporus, Poria, Portae Cutis, Portulacae Herba, Potentillae Chinensis Herba, Potentillae Discoloris Herba, Powdered Buffalo Horn Extract, Prinsepiae Nux, Propolis, Prunellae Spica, Pruni Semen, Psammosilenes Radix, Pseudolaricis Cortex, Pseudostellariae Radix, Psoraleae Fructus, Pterocephali Herba, Puerariae Lobatae Radix, Puerariae Thomsonii Radix, Pulsatillae Radix, Pyritum, Pyrolae Herba, Pyrrosiae Folium, Quisqualis Fructus, Rabdosiae Rubescentis Herba, Ranae Oviductus, Ranunculi Ternati Radix, Raphani Semen, Realgar, Rehmanniae Radix Praeparata, Rehmanniae Radix, Rhapontici Radix, Rhei Radix Et Rhizoma, Rhodiolae Crenulatae Radix Et Rhizoma, Rhododendri Daurici Folium, Rhododendri Mollis Flos, Rhubarb Extract, Rhubarb Liquid Extract, Ricini Semen, Rosae Chinensis Flos, Rosae Laevigatae Fructus, Rosae Rugosae Flos, Rubi Fructus, Rubiae Radix Et Rhizoma, Saigae Tataricae Cornu, Salvia Total Phenolic Acids, Salviae Miltiorrhizae Radix Et Rhizoma, Sanguisorbae Radix, Santali Albi Lignum, Saposhnikoviae Radix, Sappan Lignum, Sarcandrae Herba, Sargassum, Sargentodoxae Caulis, Sauropi Folium, Saururi Herba, Saussureae Involucratae Herba, Schisandrae Chinensis Fructus, Schisandrae Sphenantherae Fructus, Schizonepetae Herba Carbonisata, Schizonepetae Herba, Schizonepetae Spica Carbonisata, Schizonepetae Spica, Scolopendra, Scorpio, Scrophulariae Radix, Scutellaria Extract, Scutellariae Barbatae Herba, Scutellariae Radix, Sedi Herba, Selaginellae Herba, Semiaquilegiae Radix, Senecionis Scandentis Hebra, Sennae Folium, Sepiae Endoconcha, Serpentis Periostracum, Sesame Oil, Sesami Semen Nigrum, Setariae Fructus Germinatus, Siegesbeckiae Herba, Silybi Fructus, Sinapis Semen, Sinomenii Caulis, Sinopodophylli Fructus, Siphonostegiae Herba, Siraitiae Fructus, Smilacis Chinae Rhizoma, Smilacis Glabrae Rhizoma, Sojae Semen Germinatum, Sojae Semen Nigrum, Sojae Semen Praeparatum, Solidaginis Herba, Sophorae Flavescentis Radix, Sophorae Flos, Sophorae Fructus, Sophorae Tonkinensis Radix Et Rhizoma, Sparganii Rhizoma, Spatholobi Caulis, Spiceleaf Kernel Oil, Spirodelae Herba, Stachyuri Medulla Helwingiae Medulla, Stalactitum, Star Anise Oil, Stauntoniae Caulis Et Folium, Stellariae Herba, Stemonae Radix, Stephaniae Tetrandrae Radix, Sterculiae Lychnophorae Semen, Strychni Semen Pulveratum, Strychni Semen, Styrax, Suis Fellis Pulvis, Sulfur, Swertiae Herba, Swertiae Mileensis Herba, Syngnathus, Syringae Cortex, Talci Pulvis, Talcum, Tamaricis Cacumen, Tanshinones, Taraxaci Herba, Taxilli Herba, Tea-Seed Oil, Terminaliae Belliricae Fructus, Testudinis Carapacis Et Plastri Colla, Testudinis Carapax Et Plastrum, Tetrapanacis Medulla, Thlaspi Herba, Thunberg Fritillary Liquid Extract, Tinosporae Radix, Toatal Ginsenoside Of Ginseng Stems And Leaves, Toosendan Fructus, Torreyae Semen, Total Ginsenoside Ginseng Root, Toxicodendri Resina, Trachelospermi Caulis Et Folium, Trachycarpi Petiolus, Tribuli Fructus, Trichosanthis Fructus, Trichosanthis Pericarpium, Trichosanthis Radix, Trichosanthis Semen Tostum, Trichosanthis Semen, Trigonellae Semen, Trionycis Carapax, Tsaoko Fructus, Turpentine Oil, Turpiniae Folium, Typhae Pollen, Typhonii Rhizoma, Uncariae Ramulus Cum Uncis, Vaccariae Semen, Valerianae Jatamansi Rhizoma Et Radix, Verbenae Herba, Vespae Nidus, Vignae Semen, Violae Herba, Visci Herba, Vitex Oil, Viticis Fructus, Viticis Negundo Folium, Vladimiriae Radix, Weeping Forsythia Extract, Wenyujin Rhizoma Concisum, Xanthii Fructus, Zanthoxyli Pericarpium, Zanthoxyli Radix, Zaocys, Zedoary Turmeric Oil, Zingiberis Rhizoma Praeparatum, Zingiberis Rhizoma Recens, Zingiberis Rhizoma, Ziziphi Spinosae Semen.

In certain embodiments, the drug content further comprises an excipient. The excipient can be associated with the API, i.e., the excipient is in physical contact with the API. In certain embodiments, the API is embedded in the excipient. In certain embodiments, the API is dispersed within the excipient. In certain embodiments, the excipient is made from a water-soluble material selected from the group consisting of cocoa butter, polyethylene glycol (PEG), sucrose, glucose, galactose, fructose, xyloselactose, maltose, trehalose, sorbitol, mannitol, maltodextrins, raffinose, stachyose, fructo-oligosaccharides and a combination thereof. In certain embodiments, the excipient is made of a thermoplastic material as disclosed herein.

The drug content can be of any suitable shape and size to be loaded into the compartment. In certain embodiments, the drug content is formed in the shape of a compressed tablet, an oval tablet, a pill, or a capsulet. In certain embodiments, the shape of the drug content matches the shape of the compartment. For example, when the compartment is a pie-shape, the drug content is also of a pie-shape, e.g., to fill the compartment. In certain embodiments, the drug content is in the form of nanoparticles. In certain embodiments, the drug content is in the form of microneedles. In certain embodiments, the drug content forms a network.

In certain embodiments, when the drug content is loaded into the compartment, it is associated with the substrate, e.g., embedded or fixed in the substrate. In certain embodiments, the drug content is detachable from the substrate when loaded into the compartment. In certain embodiments, the drug content is operably linked to the compartment via covalent bond, non-covalent interactions or through a linker. Thus, the drug content and the substrate can be made separately and associate together through a covalent bond or non-covalent interactions. In certain embodiments, dosage form is made by producing the drug content and the substrate in a single process using 3D printing methods.

As used herein, the releaser refers to a structure or substance that upon contact with water or body fluid can expand in volume or generate force (e.g., by generating gas) to disintegrate the substrate, e.g., by separating the pieces of the substrate, and open the compartment. In certain embodiments, it takes the releaser after contacting water or body fluid less than 5, 10, 20, 30, 40, 50 seconds or less than 1, 2, 3, 4, 5, 10, 20, 30 mins, or less than 1, 2, 3, or 4 hours to disintegrate the substrate.

In one embodiment, the compartment has an aperture which is sealed by the releaser. The aperture can have a defined shape, e.g., a circle, a square, a triangle, etc.

In certain embodiments, the releaser is made of a hydrogel that can expand in volume after absorbing water.

In certain embodiments, the compartment has an aperture that is sealed by a semipermeable membrane. In certain embodiments, the semipermeable membrane is made from a material selected from the group consisting of cellulose acetate, ethylcellulose, ethylene-vinyl acetate copolymer and combinattions thereof.

In certain embodiments, the releaser is made of an effervescent material loaded in the compartment. In certain embodiments, the effervescent material is selected from the group consisting of citric acid, sodium carbonate, sodium bicarbonate, sodium metabisulphite, calcium carbonate and combinations thereof. In certain embodiment, at least part of the substrate is water permeable or erodible. Upon contact with water or body fluid, water penetrate into the compartment to induce the effervescent material to generate gas, thereby disintegrating the substrate and releasing the drug content from the compartment.

In another aspect, the present disclosure provides a solid pharmaceutical dosage form for multiple-pulse drug release. In one embodiment, the dosage form comprises a first substrate that forms a first compartment, wherein the first substrate comprises at least a first piece and a second piece, wherein the first piece operably links to the second piece. The dosage form contains a first drug content loaded into the first compartment. The dosage dosage form also comprises a first releaser operably linked to the first substrate which upon contact with water or body fluid is capable of separating the first and second piece to open the first compartment and release the first drug content. The dosage form further comprises a second substrate that forms a second compartment, wherein the second substrate comprises at least a third piece and a fourth piece, wherein the third piece operably links to the fourth piece. The dosage form contains a second drug content loaded into the second compartment. The dosage form has a second releaser operably linked to the second substrate which upon contact with water is capable of separating said third and fourth piece to release the second drug content. The first substrate is operably linked to the second substrate, and the first compartment is separated from the second compartment. The second releaser is accessible to water or body fluid only after the first and second pieces are separated and the first compartment is opened.

In one embodiment, the first compartment has a first aperture which is sealed by the first releaser. In one embodiment, the second compartment has a second aperture which is sealed by the second releaser. In one embodiment, the second aperture is enclosed in the first compartment.

In one embodiment, the first compartment has a first aperture that is sealed by a first plug made from water permeable or erodible material. The second compartment has a second aperture that is sealed by a second plug make from water permeable or erodible material. The second aperture is enclosed in the first compartment. The first releaser is made of effervescent material, which is loaded in the first compartment. The second releaser is made of effervescent material, which is loaded in the second compartment. Upon contact with water, the first plug is dissolved to allow water to penetrate to the first compartment. The first releaser then generates gas to disintegrate the first substrate and open up the first compartment. Only after the first compartment is opened up, the second plug is accessible to water and becomes dissolved. The water then penetrates to the second compartment, and the second releaser generates gas to disintegrate the second substrate and open up the second compartment.

In certain embodiments, the first drug content is the same as the second drug content. In certain embodiments, the first drug content is different from the second drug content.

In certain embodiments, the first releaser and the second releaser are made of the same material. In certain embodiments, the first releaser and the second releaser are made from different materials.

In certain embodiments, the first substrate stacks on the second substrate.

Manufacture of the Dosage Form

The controlled release dosage forms disclosed herein can be manufactured using any appropriate process. In certain embodiments, the dosage forms are produced using three-dimensional printing (3D printing).

As used herein, 3D printing refers to a process that produce 3D objects layer-by-layer from digital designs. The basic process of 3D printing has been described in U.S. Pat. Nos. 5,204,055; 5,260,009; 5,340,656; 5,387,380; 5,503,785; and 5,633,021. Additional U.S. patents and applications related to 3D printing include: U.S. Pat. Nos. 5,490,962; 5,518,690; 5,869,170; 6,530,958; 6,280,771; 6,514,518; 6,471,992; 8,828,411; U.S. PG Pub. Nos: 2002/0015728; 002/0106412; 2003/0143268; 2003/0198677; 2004/0005360. Reference can be made to the patents and applications listed above for a detailed description of 3D printing.

Different 3D printing methods have been developed for dosage form manufacturing in terms of raw materials, equipment and solidification. These 3D printing methods include binder deposition (see L Gibson et al. (2015) Additive Manufacring Technologies: 3D Printing, Rapid Prototyping, and Direct Digital Manufacturing. 2 ed. Springer, New York; W. E. Katstra et al. (2000) Oral dosage forms fabricated by three dimensional printing, J. Control Release 66: 1-9; W. E. Katstra et al. (2001) Fabrication of complex oral delivery forms by three dimensional printing, Dissertation in Materials Science and Engineering, Massachussetts Institute of Technology; H. Lipson et al. (2013) Fabricated: The New World of 3D printing, John Wiley & Sons, Inc.; G. Jonathan, A. Karim (2016) 3D printing in pharmaceutics: a new tool for designing customized drug delivery systems, Int. J. Pharm. 499: 376-394), material jetting (see G. Jonathan, A. Karim (2016) 3D printing in pharmaceutics: a new tool for designing customized drug delivery systems, Int. J. Pharm. 499: 376-394), extrusion (see L Gibson et al. (2015) Additive Manufacring Technologies: 3D Printing, Rapid Prototyping, and Direct Digital Manufacturing. 2 ed. Springer, New York) and photopolymerization (see F. P. Melchels et al. (2010) A review on stereolithography and its application in biomedical engineering. Biomaterials 31: 6121-30).

In certain embodiments, the dosage forms disclosed herein are manufactured using binder deposition methods. In a typical binder deposition, inkjet printers spray binder-containing liquid formulation in small droplets at precise speeds, motions and sizes onto a powder bed, which contains a layer of powders. Unbound powder severs as the support material for free-standing or porous structures. A new layer of power is then added atop, followed by the next round of binder spray. The liquid formulations inside the printer may contain a binder only, and the powder bed may contain the active ingredient with additaional excipients. Alternatively, APIs can be jetted onto powder beds as solutions or nanoparticulate suspensions.

In certain embodiments, the dosage forms disclosed herein are manufactured using extrusion methods. In an extrusion process, material is extruded from robotically-actuated nozzles. Unlike binder deposition, which requires a powder bed, extrusion methods can print on any substrate. A variety of materials can be extruded for 3D printing, including thermoplastic materials disclosed herein, pastes and colloidal suspensions, silicones and other semisolids. Typically, the thermoplastic material is melted in the 3D printer before being extruded to form the substrate. In certain embodiment, appropriate extruders include without limitation, single or twin screw extruders with the temperature within the extruder at a range from 50° C. to 180° C. and from 80° to 140° C. In general, the extrusion process can be conducted at temperatures 10° to 40° C. above the glass transition (Tg) of the thermoplastic material. Once at a suitable temperature for use in the three-dimensional printer, the thermoplastic material can be deposited to the three-dimensional printing surface. The shape and size of the substrate and the compartment fabricated by the thermoplastic material can be controlled by programing the three-dimensional printing process. (see L Gibson et al. (2015) Additive Manfacturing Technologies: 3D Printing, Rapid Prototyping, and Direct Digital Manufacturing. 2 ed. Springer, New York).

The manufacturing instructions for a print job may be generated a variety of ways, including direct coding, derivation from a solid CAD model, or other means specific to the 3D printing machine's computer interface and application software. These instructions may include information on the number and spatial placement of droplets, and on general print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the print parameters, and the material properties.

In certain embodiments, the drug content is fabricated in the same process of the matrix. In certain embodiments, the drug content is fabricated beforethe making of the matrix and loaded into the compartment during or after the matrix is fabricated.

Because of its ability of handling a range of pharmaceutical materials and control both composition and architecture locally, 3D printing is well suited to the fabrication of dosage forms with complex geometry and composition in accordance with the present invention.

The following illustrates exemplary embodiments with reference to the figures.

Figure 1B:
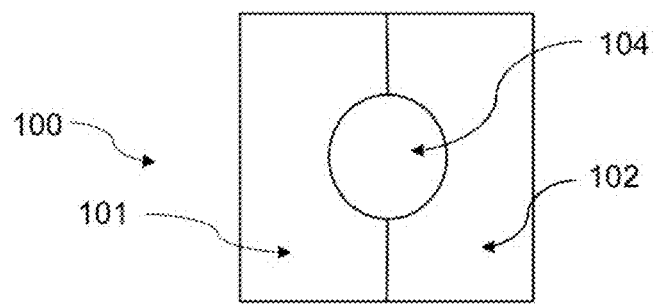
FIG. 1B shows a bottom view of the dosage form according to FIG. 1A.
Figure 1C:
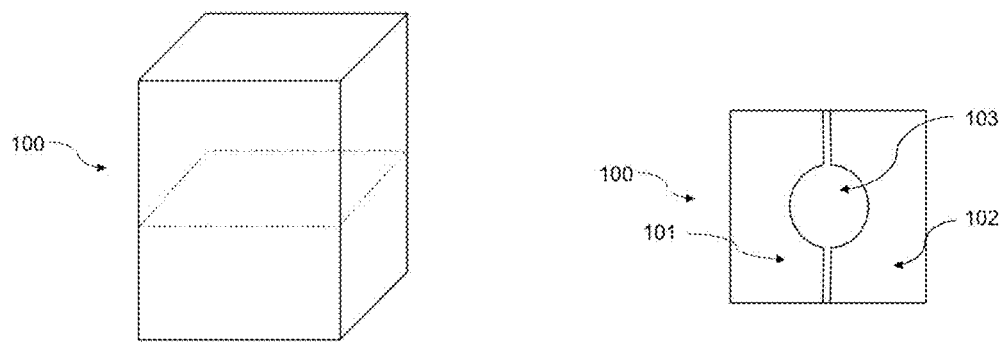
FIG. 1C shows a horizontal cross-section view of the dosage form.
Figure 1D:
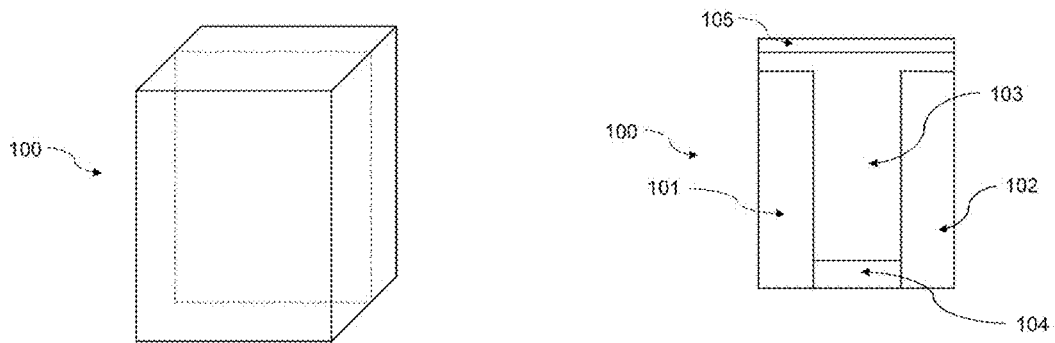
FIG. 1D shows a vertical cross-section view of the dosage form.

FIGS. 1A-1D illustrates a solid pharmaceutical dosage form according to one embodiment of the invention. Referring to FIG. 1A, the solid pharmaceutical dosage form 100 includes a first piece 101 and a second piece 102. The first piece 101 and the second piece 102 are operably linked to form a compartment 103, in which a drug content is loaded (not shown in the figure). The dosage form 100 also includes a cover 105 that seals the top end of the compartment 103. The compartment 103 also has an aperture that is sealed by a releaser 104. FIG. 1B shows a bottom view of the dosage form 100. Referring to FIG. 1B, the first piece 101 and the second piece 102 are operably linked. The compartment 103 has an aperture that is sealed by a releaser 104. FIG. 1C shows a horizontal cross sectional view of the dosage form 100. Referring to the left part of FIG. 1C, the dashed line shows the position of the cross section. Referring to the right part of FIG. 1C, the first piece 101 is operably linked to the second piece 102 through a thin connection. The compartment 103 formed by the first and seond piece is also shown. FIG. 1D shows a vertical cross section view of the dosage form 100. Referring to the left part of FIG. 1D, the dashed line shows the position of the cross section. Referring to the right part of FIG. 1D, each of the first piece 101 and the second piece 102 is operably linked to the cover 105 through a thin connection. The compartment 103 formed by the first and seond piece is also shown. The cover 105 and the releaser 104 seal the top and the bottom end of the compartment 103, respectively.

In one embodiment, the releaser 104 is made of hydrogel. Upon exposure to water, the releaser 104 expands, which breaks the connection between the first piece 101 and the second piece 102 to open up the compartment 103 and release the drug content. The opens up of the compartment can be controlled in various ways, e.g., by controlling the expansion speed of the releaser, by controlling the strength of the connection between the pieces, and by covering the releaser with a substance having appropriate solubity, etc.

Figure 2A:
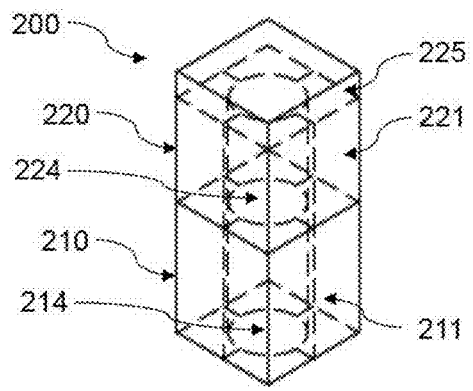
FIG. 2A shows a top perspective view of a solid pharmaceutical dosage form according to an embodiment of the invention.
Figure 2B:
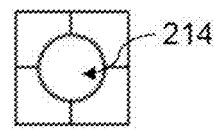
FIG. 2B shows a bottom view of the dosage form according to FIG. 2A
Figure 2C:
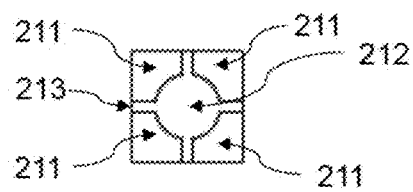
FIG. 2C shows a horizontal cross-section view of the solid pharmaceutical dosage form according to FIG. 2A.
Figure 2D:
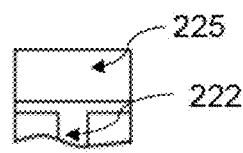
FIG. 2D shows a vertical cross-sectional view of the solid pharmaceutical dosage form according to FIG. 2A.
Figure 2D:
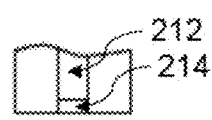

FIGS. 2A-2D illustrates a solid pharmaceutical dosage form according to another embodiment of the invention. Referring to FIG. 2A, the solid pharmaceutical dosage form 200 includes a first substrate 210 and a second substrate 220 stacking on the first substrate 210. FIG. 2B shows a bottom view of the dosage form 200. FIG. 2C shows a horizontal cross sectional view of the dosage form 200 at the middle of the first substrate 210. FIG. 2C illustrates a vertical cross sectional view of the dosage form 200. Referring to FIGS. 2A-2D, each of substrates 210 and 220 includes four pieces (211 and 221, respectively) linked through very thin material (e.g., 213) that hold the pieces together to form a first compartment 212 and a second compartment 222 in which a first drug content and a second drug content is loaded, respectively. Referring to FIGS. 2A and 2B, the first substrate 210 includes at the bottom a first releaser 214 made of a water swellable polymer, which seals the first compoartment 212 and expands to breaks up the four pieces when exposed to water or body fluid. Referring to FIGS. 2A and 2D, the second substrate 220 includes at the top a cover 225 that operably links to the pieces 221 through thin material. The second substrate 220 also includes at the bottom a second releaser 224 made of a water swellable polymer, which seals the second compoartment 222 and expands to breaks up the four pieces 221 when exposed to water or body fluid.

Figure 3A:
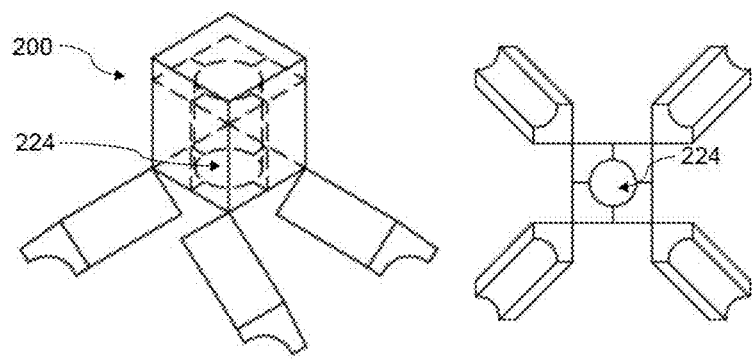
FIG. 3A shows the open up of the first compartment of a solid pharmaceutical dosage form according to FIG. 2A when exposed to water.
Figure 3B:
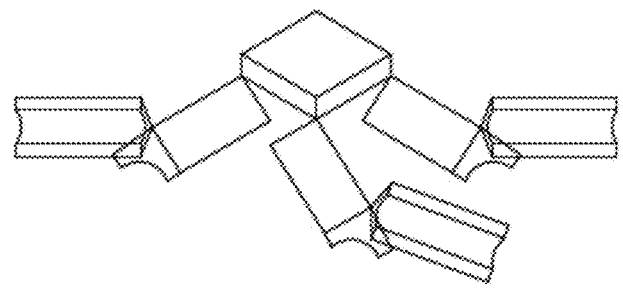
FIG. 3B shows the open up of the second compartment of the dosage form according to FIG. 2A after the first compartment opens up.

FIG. 3A-3B shows the control release of drug contents from the dosage form 200 illustrated in FIG. 2A-2D. Referring to FIGS. 3A and 3B, when the dosage form 200 is exposed to water or body fluid (e.g., after oral administration), the first releaser expands to breaks up the pieces of the first substrate and opens up the first compartment to release the first drug content. On the other hand, the second releaser 224 is enclosed in the first compartment and not accessable to water until the first compartment opens up. After the break up of the first substrate, the second releaser 224 is exposed to water and expands to breaks up the second substrate. The second drug content is then released.

Figure 4:
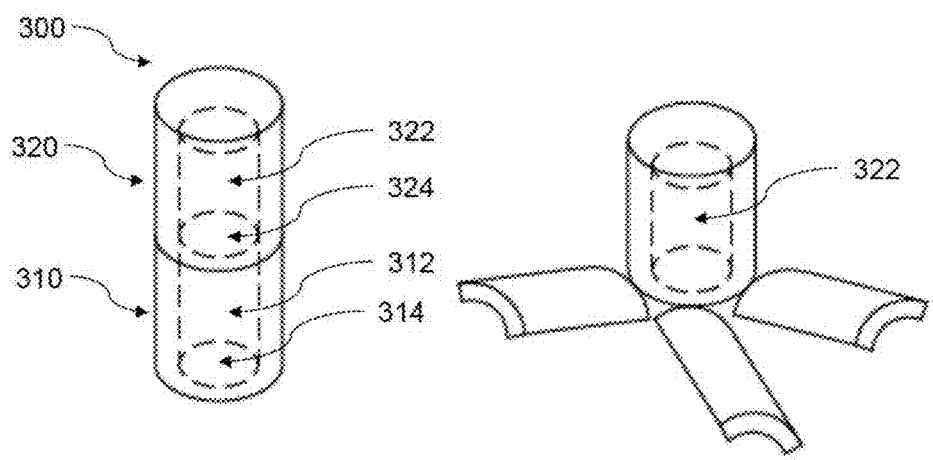
FIG. 4 shows a top perspective view of a solid pharmaceutical dosage form according to an embodiment of the invention.
Figure 5A:
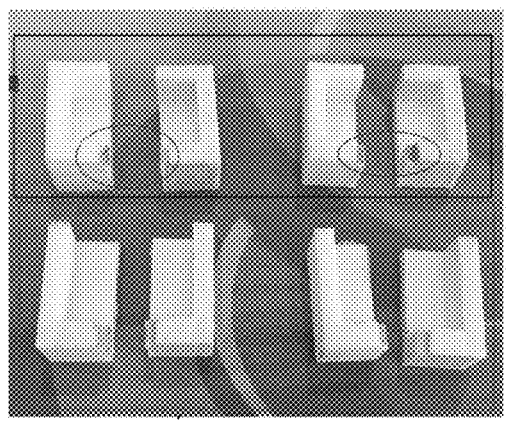
FIG. 5A shows the pieces that form the substrate of a solid pharmaceutical dosage form according to an embodiment of the invention.
Figure 5B:
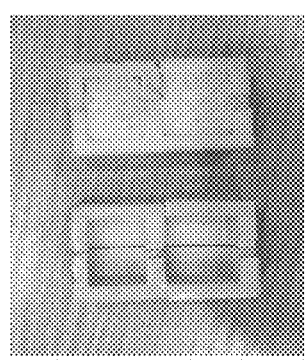
FIG. 5B shows the assembled pieces as illustrated in FIG. 5A.
Figure 5C:
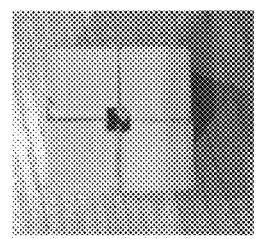
FIG. 5C shows the bottom view of the dosage form of FIGS. 5A and 5B.
Figure 5D:
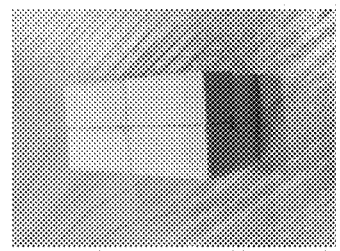
FIG. 5D shows the perspective view of the dosage form of FIG. 5A-C.

FIG. 4 shows a solid pharmaceutical dosage form according to another embodiments of the invention. In this embodiment, the dosage form 300 has a first substrate 310 and a second substrate 320 stacking on the first substrate 310. Each substrate has a shape of cylindrical column and includes three pieces linked through very thin material that hold the pieces together to form a first compartment 312 and a second compartment 322, respectively. A first drug content and a second drug content is loaded into the first compartment 312 and the second compartment 322, respectively. The first substrate 310 includes at the bottom a first releaser 314 made of a water swellable polymer. The second substrate 320 includes at the bottom a second releaser 324 make of a water sellable polymer. As the second substrate 320 stacks on the first substrate 310, the second releaser is enclosed in the first compartment. When the dosage form is exposed to water or body fluid, the first releaser 314 expands to breaks up the pieces of the first substrate 310 and opens up the first compartment 312 to release the first drug content. On the otherhand, before the first compartment 312 is opened up, the second releaser 324 is not accessable to water. After the break up of the first substrate 310, the second releaser is exposed to water and expands to breaks up the second substrate 320. The second drug content is then released.

Example

This example illustrates one dosage form that provides multiple-pulse release profile.

As shown in FIGS. 5A-5D, the dosage form has two compartments, each of which is composed of four pieces that are operably linked. The first compartment has a first aperture at the bottom that is sealed by a first plug made from water permeable or erodible material. The second compartment has a second aperture that is sealed by a second plug make from water permeable or erodible material. The second aperture is enclosed in the first compartment. The first releaser is made of effervescent material (citrate and sodium bicarbonate), which is loaded in the first compartment. The second releaser is made of citrate and sodium bicarbonate, which is loaded in the second compartment. Upon contact with water, the first plug is dissolved to allow water to penetrate to the first compartment. The first releaser then generates gas to disintegrate the first substrate and open up the first compartment. Only after the first compartment is opened up, the second plug is accessible to water and becomes dissolved. The water then penetrates to the second compartment, and the second releaser generates gas to disintegrate the second substrate and open up the second compartment.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A solid pharmaceutical dosage form comprising:
   a substrate that forms a compartment,
      wherein the substrate comprises at least a first piece and a second piece,
      wherein the first piece operably links to the second piece, and
      wherein the first piece and the second piece are not permeable to water or body fluid;
   a drug content loaded into the compartment; and
   a releaser operably linked to the substrate which upon contact with water or body fluid is capable of separating said first and second piece to release the drug content,
      wherein the compartment has an aperture which is sealed by the releaser.

2. The dosage form of claim 1, wherein the releaser comprises a hydrogel.

3. The dosage form of claim 1, wherein the substrate is made from a thermoformable material.

4. The dosage form of claim 3, wherein the thermoformable material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), poly(butyl methacrylate-co-(2-dimethylaminoethyl) methacrylate-co-methyl methacrylate) 1:2:1, poly(dimethylaminoethylmethacrylate-co-methacrylic esters), poly (ethyl acrylate-co-methyl methacrylate-cotrimethylammonioethyl methacrylate chloride), poly(methyl acrylate-comethyl methacrylate-co-methacrylic acid) 7:3:1, poly(methacrylic acid-co-methylmethacrylate) 1:2, poly (methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly (ethylene-co-vinyl acetate), ethylene-vinyl acetate copolymer, polyethylene (PE), and polycaprolactone (PCL), Eudragit RS PO, Triethyl citrate (TEC) and a combination thereof.

5. The dosage form of claim 1, wherein the substrate has a shape of a square column or a cylindrical column.

6. The dosage form of claim 1, wherein the compartment has a shape of a square column or a cylindrical column.

7. The dosage form of claim 1, wherein the drug content comprises an active pharmaceutical ingredient (API).

8. The dosage form of claim 7, wherein the API is selected from the groups consisting of local anesthetics, antiepileptic drugs and anticonvulsants, anti-alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, immunomodulators, and cosmetically active agents.

9. The dosage form of claim 7, wherein the drug content further comprises an excipient associated with the API.

10. The dosage form of claim 9, wherein the excipient is made from a water-soluble material selected from the group consisting of cocoa butter, polyethylene glycol (PEG), sucrose, glucose, galactose, fructose, xyloselactose, maltose, trehalose, sorbitol, mannitol, maltodextrins, raffinose, stachyose, fructo-oligosaccharides, polyvinylpyrrolidone-polyvinyl acetate copolymer (PVP-VA) 60/40, hydroxyl propyl cellulose (HPC), Triethyl citrate (TEC) and a combination thereof.

11. A solid pharmaceutical dosage form comprising:
a first substrate that forms a first compartment,
wherein the first substrate comprises at least a first piece and a second piece,
wherein the first piece operably links to the second piece, and
wherein the first piece and the second piece are not permeable to water or body fluid;
a first drug content loaded into the first compartment;
a first releaser operably linked to the first substrate which upon contact with water or body fluid is capable of separating the first and second piece to release the first drug content,
wherein the first compartment has a first aperture which is sealed by the first releaser;
a second substrate that forms a second compartment,
wherein the second substrate comprises at least a third piece and a fourth piece,
wherein the third piece operably links to the fourth piece, and
wherein the third piece and the fourth piece are not permeable to water or body fluid;
a second drug content loaded into the second compartment;
a second releaser operably linked to the second substrate which upon contact with water is capable of separating said third and fourth piece to release the second drug content,
wherein the second compartment has a second aperture which is sealed by the second releaser;
wherein
the first substrate is operably linked to the second substrate,
the first compartment is separated from the second compartment, and
the second releaser is accessible to water or body fluid only after the first and second pieces are separated.

12. The dosage form of claim 11, wherein the first drug content is the same as the second drug content.

13. The dosage form of claim 11, wherein the first drug content is different from the second drug content.

14. The dosage form of claim 11, wherein the first releaser and the second releaser are made of the same material.

15. The dosage form of claim 11, wherein the first releaser is made of a first material and the second releaser is made of a second material, wherein the first material is different from the second material.

16. The dosage form of claim 11, wherein the second substrate stacks on the first substrate.

* * * * *